US006485967B1

(12) United States Patent
Elliott et al.

(10) Patent No.: US 6,485,967 B1
(45) Date of Patent: *Nov. 26, 2002

(54) HUMAN NEURONAL NICOTINIC ACETYLCHOLINE RECEPTOR α6 AND β3 NUCLEIC ACID

(75) Inventors: Kathryn J. Elliott, San Diego, CA (US); Michael M. Harpold, El Cajon, CA (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/484,722

(22) Filed: Jun. 7, 1995

(51) Int. Cl.⁷ .............................. C12N 5/10; C12N 15/12
(52) U.S. Cl. ....................................... 435/325; 536/23.5
(58) Field of Search ........................... 536/23.5, 24.31; 435/240.2, 69.1, 6, 7.1, 325; 530/350

(56) References Cited

U.S. PATENT DOCUMENTS

| 4,837,148 A | 6/1989 | Cregg .......................... 435/172 |
| 4,855,231 A | 8/1989 | Stroman et al. ................ 435/68 |
| 4,859,609 A | 8/1989 | Dull et al. .................... 435/501 |
| 4,882,279 A | 11/1989 | Cregg .......................... 435/68 |
| 4,929,555 A | 5/1990 | Cregg et al. .................. 435/172 |
| 4,981,784 A | 1/1991 | Evans et al. ................... 435/6 |
| 5,024,939 A | 6/1991 | Gorman ......................... 435/69 |
| 5,071,773 A | 12/1991 | Evans et al. ................... 436/501 |
| 5,091,518 A | 2/1992 | Sucov et al. ................... 536/27 |
| 5,369,028 A | 11/1994 | Harpold et al. ................ 435/252 |
| 5,371,188 A | 12/1994 | Heinemann et al. ........... 530/350 |
| 5,386,025 A | 1/1995 | Jay et al. ...................... 536/24 |
| 5,401,629 A | 3/1995 | Harpold et al. ................ 435/6 |
| 5,436,128 A | 7/1995 | Harpold et al. ................ 435/6 |

FOREIGN PATENT DOCUMENTS

| EP | 0325849 | 8/1989 |
| WO | 8803168 | 5/1988 |
| WO | 8909834 | 10/1989 |
| WO | 9010648 | 9/1990 |
| WO | 9106677 | 5/1991 |
| WO | 9115602 | 10/1991 |
| WO | 9202639 | 2/1992 |
| WO | 9513299 | 5/1995 |

OTHER PUBLICATIONS

Lamar et al. (1990) Abstracts 20$^{th}$ Annual Meeting for Society for Neuroscience 16: 681.*
Brammar. ELG CAT nACHR. in the Ion Channel, Facts Book (Ed. by E. Lonley) 1996 Academic Press Inc, San Diego, CA, pp. 234–292.*

J. Boulter (1993) Genbank. Accession No. L08227.*
EMBL Databank Accession No. X68275 (Sep. 22, 1992), P. Tarroni (1992).
PIR 38 Databank Accession No. S27274 (Tarroni et al. 1992)).
Grenningloh et al., Alpha subunit variants of the human glycine receptor: primary structures, functional expression and chromosomal localization of the corresponding genes, *EMBO J.* 9(3):771–776 (1990).
Lin et al., Differential fluorescent staining of human chromosomes with daunomycin and adriamycin—the D–bands, *Science* 190:61–63 (1975).
Williams et al., Structure and functional expression of $a_1$, $a_2$, and β subunits of a novel human neuronal calcium channel subtypes, *Neuron* 8:71–84 (1992).
Akong et al., Characterization of nicotinic acetylcholine receptors in a human neuroblastoma cell line, *FASEB J.*, 4(3):A737 (1990).
Alam et al.,Reporter genes: Application to the study of mammalian gene transcription, *Anal. Biochem.* 188:245–254 (1990).
Albuquerque et al., Neuronal nicotinic receptors: Function, modulation and structure, *Seminars in the Neurosciences* 7:91–101 (1995).
Allard, et al., Sequence of the gene encoding the human M1 muscarinic acetylcholine receptor, *Nucl. Acids Res.* 15:10604 (1987).
Alton and Vapnek, Nucleotide sequence analysis of the chloramphenicol resistance transposon Tn9, *Nature* 282:864–869 (1979).
Anand et al., Nucleotide sequence of the human nicotinic acetylcholine receptor $β_2$ subunit gene, *Nucleic Acids Res.* 18(14):4272 (1990).
Anand et al., Neuronal nicotinic acetylcholine receptors expressed in Xenopus oocytes have a pentameric quaternary structure, *J. Biol. Chem.* 266(17):11192–11198 (1991).
Baldwin et al., Cloning of the luciferase structural genes from *Vibrio harveyi* and expression of bioluminescence in *Escherichia coli*, *Biochemistry* 23:3663–3667 (1984).
Ballivet et al., Electrophysiology of a chick neuronal nicotinic acetylcholine receptor expressed in Xenopus oocytes after cDNA injection, *Neuron* 1:847–852 (1988).
Beeson et al., The human muscle nicotinic acetylcholine receptor α–subunit exists as two isoforms: a novel exon, *EMBO J.* 9(7):2101–2106 (1990).

(List continued on next page.)

Primary Examiner—Michael Pak
(74) Attorney, Agent, or Firm—Vineet Kohli; Jack L. Tribble

(57) ABSTRACT

DNA encoding human neuronal nicotinic acetylcholine receptor alpha and beta subunits, mammalian and amphibian cells containing said DNA, methods for producing alpha and beta subunits and recombinant (i.e., isolated or substantially pure) alpha subunits (specifically $α_6$) and beta subunits (specifically $β_3$) are provided. In addition, combinations of a plurality of subunits (i.e., one or more of as $α_1$, $α_2$, $α_3$, $α_4$, $α_5$, $α_6$ and/or $α_7$ subunits in combination with one or more of $β_3$ subunits are provided.

43 Claims, 2 Drawing Sheets

OTHER PUBLICATIONS

Bertrand et al., Unconventional pharmacology of a neuronal nicotinic receptor mutated in the channel domain, *Proc. Natl. Acad. Sci. USA* 89:1261–1265 (1992).

Bertrand and Changeux, Nicotinic receptor: An allosteric protein specialized for intercellular communication, *Seminars in the Neurosciences* 7:75–90 (1995).

BIOSIS abstract #87125524, Bartel et al., Growth factors and membrane depolarization activate distinct programs of early response gene expression dissociation of fos and jun induction, *Genes Dev.* 3(3):304–313 (1989).

BIOSIS abstract # 88119253, Levy et al., Cytoplasmic activation of ESGF3 the positive regulator of interferon–alpha–stimulated transcription reconstituted in vitro, *Genes Dev.* 3(9):1362–1371 (1989).

BIOSIS abstract # 88127139, Nishizuka et al., The family of protein kinase C for signal transduction, *J. Am. Med. Assoc.* 262(13):1826–1833 (1989).

Blackshear et al., Protein kinase C–dependent and –independent pathways of proto–oncogene induction in human astrocytoma cells, *J. Biol. Chem.* 262(16):7774–7781 (1987).

Blanchard et al.,The regulatory stategiesof c–myc and c–fos proto–oncogenes share some common mechanisms, *Biochimie* 70:877–884 (1988).

Bonner et al., Cloning and expression of the human and rat m5 muscarinic acetylcholine receptor genes, *Neuron* 1:403–410 (1988).

Bonnieu et al., Requirements for c–fos mRNA down regulation in growth stimulated murine cells, *Oncogene* 4:881–888 (1989).

Bouche, Basic fibroblast growth factor enters the nucleolus and stimulates the transcription of ribosomal genes in ABAE cells undergoing $G_0$–$G_1$ transition, *Proc. Natl. Acad. Sci. USA* 84:6770–6774 (1987).

Boulter et al., Isolation of a cDNA clone coding for a possible neural nicotinic acetylcholine receptor α–subunit, *Nature* 319:368–374 (1986).

Boulter et al., Functional expression of two neuronal nicotinic acetylcholine receptors from cDNA clones identifies a gene family, *Proc. Natl. Acad. Sci. USA* 84:7763–7767 (1987).

Boulter et al., α3, α5, and β4: Three members of the rat neuronal nicotinic acetylcholine receptor–related gene family form a gene cluster, *J. Biol. Chem.* 265:4472–4482 (1990).

Boulter et al., Rat nicotinic acetylcholine receptor alpha 6 mRNA sequence, unpublished (1993) GENBANK Accession #L08227.

Briggs et al., Human α7 nicotinic acetylcholine receptor responses to novel ligands, *Neuropharmacology* 34:583–590 (1995).

Bunzow et al., Cloning and expression of a rat $D_2$ dopamine receptor cDNA, *Nature* 336:783–787 (1988).

Changelian et al., Structure of the NGFI–A gene and detection of upstream sequences responsible for its transcriptional induction by nerve growth factor, *Proc. Natl. Acad. Sci. USA* 86:377–381 (1989).

Chavez–Noriega et al., Characterization of recombinant human neuronal nicotinic ACH receptors expressed in HEK293 cells and Xenopus oocytes, *Soc. Neurosci. Abstr.* (1995).

Chini et al., Neuronal–type α–bungarotoxin receptors and the $α_5$–nicotinic receptor subunit gene are expressed in neuronal and nonneuronal human cell lines, *Proc. Natl. Acad. Sci. USA* 89:1572–1576 (1992).

Chini et al., Molecular cloning and chromosomal localization of the human $α_7$–nicotinic receptor subunit gene (CHRNA7), *Genomics* 19:379–381 (1994).

Choi et al., Labeling studies of photolabile philanthotoxins with nicotinic acetylcholine receptors: Mode of interaction between toxin and receptor, *Chemistry & Biology* 2:23–32 (1995).

Clarke, The fall and rise of neuronal α–bungarotoxin binding proteins, *Trends Pharacol. Sci.* 13:407–413 (1992).

Claudio et al., Genetic reconstitution of functional acetylcholine receptor channels in mouse fibroblasts, *Science* 238:1688–1694 (1987).

Clementi et al., Pharmacological characterization of cholinergic receptors in a human neuroblastoma cell line, *J. Neurochem.* 47(1):291–297 (1986).

Cleveland et al., Number and evolutionary conservation of the α– and β–tubulin and cytoplasmic β– and γ–actin genes using specific cloned cDNA probes, *Cell* 20:95–105 (1980).

Cohen et al., Regions of β2 and β4 responsible for differences between the steady state dose–response relationships of the α3β2 and α3β4 neuronal nicotinic receptors, *J. Gen. Physiol.* 105:745–764 (1995).

Collins et al., cAMP stimulates transcription of the $β_2$–adrenergic receptor gene in response to short–term agonist exposure, *Proc. Natl. Acad. Sci. USA* 86:4853–4857 (1989).

Comb et al., A cyclic AMP–and phorbol ester–inducible DNA element, *Nature* 323:353–356 (1986).

Conroy et al., The α5 gene product assembles with multiple acetylcholine receptor subunits to form distinctive receptor subtypes in brain, *Neuron* 9:679–691 (1992).

Conroy and Berg, Neurons can maintain multiple classes of nicotinic acetylcholine receptors distinguished by different subunit compositions, *J. Biol. Chem.* 270(9):4424–4431 (1995).

Conti–Tronconi et al., Brain and muscle nicotinic acetylcholine receptors are different but homologous proteins, *Proc. Natl. Acad. Sci. USA* 82:5208–5212 (1985).

Cooper et al., Pentameric structure and subunit stoichiometry of a neuronal nicotinic acetylcholine receptor, *Nature* 350:235–238 (1991).

Cordon–Cardo et al., The trk tyrosine protein kinase mediates the mitogenic properties of nerve growth factor and neurotropin–3, *Cell* 66:173–183 (1991).

Cotecchia et al., Multiple second messenger pathways of a α–adrenergic receptor subtypes expressed in eukaryotic cells, *J. Biol. Chem.* 265(1):63–69 (1990).

Couturier et al., A neuronal nicotinic acetylcholine receptor subunit (α7) is developmentally regulated and forms a homo–oligomeric channel blocked by α–BTX, *Neuron* 5:847–856 (1990).

Cross et al., Enhancement by 5–hydroxytryptamine and analogues of desensitization of neuronal and muscle nicotinic receptors expressed in Xenopus oocytes, *Br. J. Pharmacol.* 114:1636–1640 (1995).

Curran et al., Barium modulates c–fos expression and post–translational modification, *Proc. Natl. Acad. Sci. USA* 83:8521–8524 (1986).

Curran et al., FBJ murine osteosarcoma virus: Identification and molecular cloning of biologically active proviral DNA, *J. Virology* 44(2):674–682 (1982).

Dascal, The use of Xenopus oocytes for the study of ion channels, *CRC Crit. Rev. Biochem.* 22(4):317–387 (1987).

Deneris et al., Primary structure and expression of β2: A novel subunit of neuronal nicotinic acetylcholine receptors, *Neuron* 1:45–54 (1988).

Deneris et al., Pharmacological and functional diversity of neuronal nicotinic acetylcholine receptors, *Trends Pharmacol. Sci.* 12:34–40 (1991).

Deneris et al., $\beta_3$: A new member of nicotinic acetylcholine receptor gene family is expressed in brain, *J. Biol. Chem.* 264(11):6268–6272 (1989).

Denhardt, A membrane–filter technique for the detection of complementary DNA, *Biochem. Biophys. Res. Commun.* 23:641–646 (1966).

Deschamps et al., Identification of a transcriptional enhancer element upstream from the proto–oncogen fos, *Science* 230:1174–1177 (1985).

Devreotes, *Dictyostelium discoideum*: A model system for cell–cell interactions in development, *Science* 245:1054–1058 (1989).

deWet et al., Firefly luciferase gene: Structure and expression in mammalian cells, *Mol. Cell. Biol.* 7:725–737 (1987).

Didier et al., Characterization of nicotinic acetylcholine receptors expressed in primary cultures of cerebellar granule cells, *Mol. Brain Res.* 30:17–28 (1995).

Dixon et al., Cloning of the gene and cDNA for mammalian β–adrenergic receptor and homology with rhodopsin, *Nature* 321:75–79 (1986).

Doolittle, *Of URFS and ORFS. A Primer on How to Analyze Derived Amino Acid Sequences*, selected pages, University Science Books, Mill Valley, CA (1986).

Doucette–Stamm et al., Cloning and sequence of the human α7 nicotinic acetylcholine receptor, *Drug Development Research* 30:252–256 (1993).

Duvoisin et al., The functional diversity of the neuronal nicotinic acetylcholine receptors is increased by a novel subunit: β4, *Neuron* 3:487–496 (1989).

Elliott et al., Cloning and functional expression of human neuronal nicotinic acetylcholine receptor subunits α2, α3, α4, α7, β2 and β4, *Soc. Neurosci. Abstr.* 19(1–3):69 (1993).

Ellis et al., Replacement of insulin receptor tyrosine residues 1162 and 1163 compromises insulin–stimulated kinase activity and uptake of 2–deoxyglucose, *Cell* 45:721–732 (1986).

Ellis et al., Sequence and expression of mRNAs encoding the $\alpha_1$ and $\alpha_2$ subunits of a DHP–sensitive calcium channel, *Science* 241:1661–1664 (1988).

EMBASE abstract # 87032747, Gonda et al., A molecular basis for growth regulation in normal and neoplastic hemopoiesis, *Cancer Rev.(Denmark)* 3:58–90 (1986).

EMBASE abstract # 90361366, Roux et al., Nuclear localization of c–fos, but not v–fos proteins, is controlled by extracellular signals, *Cell* 63(2):341–351 (1990).

EMBASE abstract #90191445, Kouzarides et al., Behind the fos and jun leucine zipper, *Cancer Cells* 1(3):71–76 (1989).

Engebrecht and Silverman, Identification of genes and gene products necessary for bacterial bioluminescence, *Proc. Natl. Acad. Sci. USA* 1:4154–4158 (1984).

Fanger et al., Differential expression of sodium channels and nicotinic acetylcholine receptor channels in nnr variants of the PC12 pheochromocytoma cell line, *J. Membrane Biol.* 144:71–80 (1995).

Figl et al., Regions of β4•β2 subunit chimeras that contribute to the agonist selectivity of neuronal nicotinic receptors, *FEBS Lttrs.* 308(3):245–248 (1992).

Fink et al., The CGTCA sequence motif is essential for biological activity of the vasoactive intestinal peptide gene cAMP–regulated enhancer, *Proc. Natl. Acad. Sci. USA* 85:6662–6666 (1988).

Firtel et al., G protein linked signal transduction pathways in development: Dictyostelium as an experimental system, *Cell* 58:235–239 (1989).

Fornasari et al., Molecular cloning of human neuronal nicotinic receptor $\alpha_3$–subunit, *Neurosci. Lttrs.* 111:351–356 (1990).

Frielle et al., Cloning of the cDNA for the human $\beta_1$–adrenergic receptor, *Proc. Natl. Acad. Sci. USA* 84:7920–7924 (1987).

Galzi et al., Mutations in the channel domain of a neuronal nicotinic receptor convert ion selectivity from cationic to anionic, *Nature* 359:500–505 (1992).

Galzi and Changeux, Neuronal nicotinic receptors: Molecular organization and regulation, *Neuropharmacology* 34(6):563–582 (1995).

Gautam et al., A G protein gamma subunit shares homology with ras proteins, *Science* 244:971–974 (1989).

Gilman, G proteins: Transducers of receptor–generated signals, *Ann. Rev. Biochem.* 56:615–649 (1987).

Goldman et al. Members of a nicotinic acetylcholine receptor gene family are expressed in different regions of the mammalian central nervous system, *Cell* 48:965–973 (1987).

Gopalkrishnan et al., Stable expression and pharmacological properties of the human $\alpha_7$ nicotinic acetylcholine receptor, *Eur. J. Pharmacol.* 290:237–246 (1995).

Gorman et al., Recombinant genomes which expresses chloramphenicol acetyltransferase in mammalian cells, *Mol. Cell. Biol.* 2(9):1044–1051 (1982).

Gotti et al., Acetylcholine operated ion channel and α–bungarotoxin binding site in a human neuroblastoma cell line reside on different molecules, *Biochem. Biophys. Res. Commun.* 137(3):1141–1147 (1986).

Goyal, Muscarinic receptor subtypes, *N. Engl. J. Med.* 321(15):1022–1029 (1989).

Green berg et al., Stimulation of neuronal acetylcholine receptors induces rapid gene transcription, *Science* 234:80–83 (1986).

Groebe et al., α–connotoxins selectively inhibit one of the two accetylcholine binding sites of the nicotinic receptors, *Mol. Pharmacol.* 48:105–111 (1995).

Hall et al., Expression and regulation of *Escherichia coli lacZ* gene fusions in mammalian cells, *J. Molec. Appl. Genet.* 2:101–109 (1983).

Halvorsen et al., Affinity labeling of neuronal acetylcholine receptor subunits with an α–neurotoxin that blocks receptor function, *J. Neurosci.* 7(8):2547–2555 (1987).

Hamill et al., Improved patch–clamp techniques for high–resolution current recording from cells and cell–free membrane patches, *Pflugers Arch.* 391:85–100 (1981).

Herschman, Extracellular signals, transcriptional responses and cellular specificity, *Trends Biochem. Sci.* 14:455–458 (1989).

Hollman et al., Cloning by functional expression of a member of the glutamate receptor family, *Nature* 342:643–648 (1989).

Horwitz et al., Muscarinic receptor stimulation increases inositol–phospholipid metabolism and inhibits cyclic AMP accumulation in PC12 cells, *J. Neurochem.* 53:197–204 (1989).

Howard et al., Expression of nicotinic acetylcholine receptors and subunit mRNA transcripts in cultures of neural crest cells, *Dev. Biol.* 170:479–495 (1995).

Hussy et al., Agonist and antagonist effects of nicotine on chick neuronal nicotinic receptors are defined by $\alpha$ and $\beta$ subunits, *J. Neurophysiol.* 72(3):1317–1326 (1994).

Ishikawa et al., Acetylcholine receptors of human skeletal muscle: A species difference detected by snake neurotoxins, *Brain Res.* 346:82–88 (1985).

Jay et al., Primary structure of the $\gamma$ subunit of the DHP–sensitive calcium channel from skeletal muscle, *Science* 248:490–492 (1990).

Johnson et al., Expression and structure of the human NGF receptor, *Cell* 47:545–554 (1986).

Julius et al., Molecular characterization of a functional cDNA encoding the serotonin 1c receptor, *Science* 241:558–564 (1988).

Julius et al., The 5HT2 receptor defines a family of structurally distinct but functionally conserved serotonin receptors, *Proc. Natl. Acad. Sci. USA* 87:928–932 (1990).

Kayano et al., Primary structure of rat brain sodium channel III deduced from the cDNA sequence, *FEBS Lttrs.* 228:187–194 (1988).

Klein et al., A chemoattractant receptor controls development in *Dictyostelium discoideum*, *Science* 241:1467–1472 (1988).

Kobilka et al., Cloning, sequencing, and expression of the gene coding for the human platelet $\alpha_2$–adrenergic receptor, *Science* 238:650–656 (1987).

Kobilka et al., An intronless gene encoding a potential member of the family of receptors coupled to guanine nucleotide regulatory proteins, *Nature* 329:75–79 (1987).

Kurosaki et al., Funtional properties of nicotinic acetylcholine receptor subunits expressed in various combinations, *FEBS Lttrs.* 214(2):253–258 (1987).

Lamb et al., Demonstration in living cells of an intragenic negative regulatory element within the rodent c–fos gene, Cell, 61:485–496 (1990).

Lambert et al., Muscarinic receptor binding characteristics of a human neorublastomas SK–N–SH and its clones SH–SY5Y and SH–EP1, *Eur. J. Pharmacol.* 165:71–77 (1988).

Larsson et al., In vitro binding of $^3$H–acetylcholine to nicotinic receptors in rodent and human brain, *J. Neural Transm.* 69:3–18 (1987).

Lathe, Synthetic oligonucleotide probes deduced from amino acid sequence data theoretical and practical considerations, *J. Mol. Biol.* 183:1–12 (1984).

Levitan et al., Structural and functional basis for $GABA_A$ receptor heterogeneity, *Nature* 335:76–79 (1988).

Listerud et al., Functional contribution of neuronal AChR subunits revealed by antisense oligonucleotides, *Science* 254:1518–1521 (1991).

Lloyd et al., SIB–1765F, a novel nicotinic agonist: Profile in models of extrapyramidal motor dysfunction, *Soc. Neurosci. Abstr.* (1995).

Lobron et al., Cellular distribution in the rat telencephalon of mRNAs encoding for the $\alpha 3$ and $\alpha 4$ subunits of the nicotinic acetylcholine receptor, *Mol. Brain Res.* 30:70–76 (1995).

London et al., In vivo labeling of nicotinic acetylcholine receptors in brain with [$^3$H]epibatidine, *Eur. J. Pharmacol.* 278:R1–R2 (1995).

Luetje et al., Both $\alpha$– and $\beta$–subunits contribute to the agonist sensitivity of neuronal nicotinic acetylcholine receptors, *J. Neurosci.* 11(3):837–845 (1991).

Lukas, Pharmacological distinctions between functional nicotinic acetylcholine receptors on the PC12 rat pheochromocytoma and the TE671 human medulloblastoma, *J. Pharmacol. Exp. Therap.* 251(1):175–182 (1989).

Lukas et al., Characterization of nicotinic acetylcholine receptors expressed by cells of the SH–SY5Y human neuroblastoma clonal line, *Mol. Cell. Neurosci.* 4(1):1–12 (1993).

Marshall et al., Sequence and functional expression of a single $\alpha$ subunit of an insect nicotinic acetylcholine receptor, *EMBO J.* 9(13):4391–4398 (1990).

Marullo et al., Expression of human $\beta 1$ and $\beta 2$ adrenergic receptors in *E. coli* as a new tool for ligand screening, *Bio/Technology* 7:923–927 (1989).

Matter–Sadzinski et al., Neuronal specificity of the $\alpha 7$ nicotinic acetylcholine receptor promoter develops during morphogenesis of the central nervous system, *EMBO J.* 11(12):4529–4538 (1992).

Mauron et al., Structure of chicken genes encoding the nicotinic acetylcholine receptor subunits and their variants, *Soc. Neurosci. Abstr.* 17 (1991).

McAllister et al., Establishment of a human medulloblastoma cell line, *Int. J. Cancer* 20:206–212 (1977).

McKinnon, D., Isolation of a cDNA clone coding for a putative second potassium channel indicates the existence of a gene family, *J. Biol. Chem.* 264:8230–8236 (1989).

Mechti et al., Sequence requirements for premature transcription arrest within the first intron of the mouse c–fos gene, *Mol. Cell Biol.* 11(5):2832–2841 (1991).

Menzaghi et al., SIB–1765F: A novel nicotinic agonist with locomotor stimulant properties in rats, *Soc. Neurosci. Abstr.* (1995).

Michel et al., PC12 phaeochromocytoma cells contain an atypical muscarinic receptor binding site, *Br. J. Pharmacol.* 97:914–920 (1989).

Monteggia et al., Cloning and transient expression of genes encoding the human $\alpha 4$ and $\beta 2$ neuronal nicotinic acetylcholine receptor (nAChR) subunits, *Gene* 155:189–193 (1995).

Montminy et al., Identification of a cyclic–AMP–responsive element within the rat somatostatin gene, *Proc. Natl. Acad. Sci. USA* 83:6682–6686 (1986).

Morgan et al., Stimulus–transcription coupling in neurons: Role of cellular immediate–early genes, *Trends Neurosci,* 12(11):459–462 (1989).

Nash et al., Molecular cloning of human neuronal nicotinic acetylcholine receptor subunits, *Neurobiol. Neurochem.* 4(7):A2153 (1990).

Nash et al., Molecular cloning and expression of human neuronal nicotinic acetylcholine receptor subunits, *Soc. Neurosci. Abstr.* 16:10 (1990).

Nef et el., Genes expressed in the brain define three distinct neuronal nicotinic acetylcholine receptors, *EMBO J.* 7(3):595–601 (1988).

Nielsen et al., A highly sensitive, mixed assay for chloramphenicol acetyltransferase activity in transfected cells, *Anal. Biochem.* 179:19–23 (1989).

Noda et al., Expression of functional sodium channels from cloned cDNA, *Nature* 322:826–828 (1986).

Noda et al., Existence of distinct sodium channel messenger RNAs in rat brain, *Nature* 320:188–192 (1986).

Nordeen, Luciferase reporter gene vectors for analysis of promoters and enhancers, *Bio Techniques* 6(5):454–456 (1988).

Nutter and Adams, Monovalent and divalent cation permeability and block of neuronal nicotinic receptor channels in rat parasympathetic ganglia, *J. Gen. Physiol.* 105:701–723 (1995).

Ortells and Lunt, Evolutionary history of the ligand–gated ion–channel superfamily of receptors, *Trends Neurosci.* 18(3):121–127 (1995).

Ostermann et al., Cellular expression of $\alpha 4$ subunit mRNA of the nicotinic acetylcholine receptor in the developing rat telencephalon, *Neurosci. Lttrs.* 192:21–24 (1995).

Papke et al., The role of the $\beta_4$—subunit in determining the kinetic properties of rat neuronal nicotinic acetylcholine $\alpha_3$—receptors, *J. Physiol.* 440:95–112 (1991).

Patrick et al., Acetylcholine receptor metabolism in a nonfusing muscle cell line, *J. Biol. Chem.* 252(6):2143–2153 (1977).

Peng et al., Human $\alpha 7$ acetylcholine receptor: Cloning of the $\alpha 7$ subunit from the SH–SY5Y cell line and determination of pharmacological properties of native receptors and functional $\alpha 7$ homomers expressed in Xenopus oocytes, *Mol. Pharmacol.* 46:546–554 (1994) (GENBANK accession #70297 submitted Feb. 4, 1993, publicly availble Jun. 1, 1994).

Peralta et al., Distinct primary structures, ligand–binding properties and tissue–specific expression of four human muscarinic acetylcholine receptors, *EMBO J.* 6(13):3923–3929 (1987).

Peralta et al., Differential regulation of PI hydrolysis and adenylyl cyclase by mascarinic receptor subtypes, *Nature*, 334:434–437 (1988).

Picciotto et al., Abnormal avoidance learning in mice lacking functional high–affinity nicotine receptor in the brain, *Nature* 374:65–67 (1995).

Pritchett et al., Importance of a novel $GABA_A$ receptor subunit for benzodiazepine pharmacology, *Nature*, 338:582–585 (1989).

Quik et al., Neuronal nicotinic $\alpha$–bungarotoxin sites, *Can. J. Physiol. Pharmacol.* 66:971–979 (1988).

Rao et al., In vitro characterization of SIB–1765F, a novel nicotinic agonist, *Soc. Neurosci. Abstr.* (1995).

Receptor Genetics, Inc. (file correspondence with SIBIA).

Revah et al., Mutations in the channel domain alter desensitization of a neuronal nicotinic receptor, *Nature* 353:846–849 (1991).

Riabowol et al., The catalytic subunit of cAMP–dependent protein kinase induces expression of genes containing cAMP–responsive enhancer elements, *Nature* 336:83–86 (1988).

Ruth et al., Primary structure of the $\beta$ subunit of the DHP–sensitive calcium channel from skeletal muscle, *Science*, 245:1115–1118 (1989).

Sacaan et al., Effect of (±)–epibatidine on the release of catecholamines: Biochemical and behavioral evidence in rats, *Soc. Neurosci. Abstr.* (1995).

Sambrook et al., *Molecular Cloning. A Laboratory Manual*, 2d Ed., Cold Spring Harbor Laboratory Press (1989).

Sargent, The diversity of neuronal nicotinic acetylcholine receptors, *Annu. Rev. Neurosci.* 16:403–443 (1993).

Sassone–Corsi et al., Induction of proto–oncogene fos transcription through the adenylate cyclase pathway: characterization of a cAMP–responsive element, *Genes Dev.* 2:1529–1538 (1988).

Schilling et al., Regulation of a fos–lacZ fusion gene: A paradigm for quantitative analysis of stimulus–transcription coupling, *Proc. Natl. Acad. Sci. USA* 88:5665–5669 (1991).

Schoepfer et al., The human medulloblastoma cell line TE671 expresses a muscle–like acetylcholine receptor, *FEBS Lttrs.* 226:(2):235–240 (1988).

Schoepfer et al., cDNA clones coding for the structural subunit of a chicken brain nicotinic acetylcholine receptor, *Neuron* 1:241–248 (1988).

Schoepfer et al., Brain $\alpha$–bungarotoxin binding protein cDNAs and MAbs reveal subtypes of this branch of the ligand–gated ion channel gene superfamily, *Neuron* 5:35–48 (1990).

Schoepfer et al., *Molecular Biology of Neuroreceptors and Ion Channels* Maelicke, A. (Ed.), NATO–ASI Series, Springer Vergal, Heidelberg (1989).

Schofield et al., Sequence and functional expression of the $GABA_A$ receptor shows a ligand–gated receptor super–family, *Nature* 328:221–227 (1987).

Séguéla et al., Molecular cloning, functional properties, and distribution of rat brain $\alpha_7$: A nicotinic cation channel highly permeable to calcium, *J. Neurosci.* 13(2):596–604 (1993).

Serra et al., The intact human neuroblastoma cell (SH–SY5Y) exhibits high–affinity [$^3$H]pirenzepine binding associated with hydrolysis of a phosphatidylinositols, *J. Neurochem.* 50:1513–1521 (1988).

Serra et al., Phorbol esters alter muscarinic receptor binding and inhibit polyphosphoninositide breakdown in human neuroblastoma (SH–SY5Y) cells, *Biochem. Biophys. Res. Comm.* 140:160–166 (1988).

Sheng et al., The regulation and function of c–fos and other immediate early genes in the nervous system, *Neuron* 4:477–485 (1990).

Shivers, B.D., Two novel $GABA_A$ receptor subunits exist in distinct neuronal subpopulations, *Neuron* 3:327–337 (1989).

Short et al., Characterization of the phosphoenolpyruvate carboxykinase (GTP) promoter–regulatory region, *J. Biol. Chem.* 261:9721–9726 (1986).

Stauderman et al., Characterization of recombinant human neuronal nicotinic acetylcholine receptor subtypes $\alpha 4\beta 4$ and $\alpha 2\beta 4$ stably expressed in HEK293 cells, *Soc. Neurosci. Abstr.* (1995).

Stillam et al., Replication and supercoiling of simian virus 40 DNA in cell extracts from human cells, *Mol. Cell.Biol.* 5:2051–2060 (1985).

Stormann et al., Molecular cloning and expression of a dopamine D2 receptor from human retina, *Molec. Pharm.* 37:1–6 (1990).

Strader et al., Structural basis of $\beta$–adrenergic receptor function, *FASEB J.* 3:1825–1832 (1989).

Stroud et al., Nicotinic acetylcholine receptor superfamily of ligand–gated ion channels, *Biochemistry* 29(50):11009–11023 (1990).

Stumpo et al., Identification of c–fos sequences involved in induction by insulin and phorbol esters, *J. Biol. Chem.* 263(4):1611–1614 (1988).

Subramani et al., Expression of the mouse dihydrofolate reductase complementary deoxyribonucleic acid in simian virus 40 vectors, *Mol. Cell Biol.* 1:854–864 (1981).

Sugaya et al., Nicotinic acetylcholine receptor subtypes in human frontal cortex: Changes in Alzheimer's disease, *J. Neurosci. Res.* 27:349–359 (1990).

Talib et al., Differential expression of human nicotinic acetylcholine receptor α subunit variants in muscle and non–muscle tissues, *Nucleic Acids Res.* 21(2):233–237 (1993).

Tanabe et al., Primary structure of the receptor for calcium channel blockers from skeletal muscle, *Nature* 328:313–318 (1987).

Tarroni et al., Neuronal–type nicotinic receptors in human neuroblastoma and small–cell lung carcinoma cell lines, *FEBS Lttrs.* 312(1):66–70 (1992) (EMBL Accession No. submitted by P. Tarroni Sep. 22, 1992).

Tempel et al., Cloning of a probable potassium channel gene from mouse brain, *Nature* 332:837–839 (1988).

Toh et al., Isolation and characterization of a rat liver alkaline phosphatase gene, *Eur. J. Biochem.* 182:231–238 (1989).

Turchi et al., Effects of nicotinic acetylcholine receptor ligands on behavioral vigilance in rats, *Psychopharmacology* 118:195–205 (1995).

Urlaub et al., Effect of gamma rays at the dihydrofolate reductase locus: Deletions and inversions, *Somatic Cell. Molec. Genet.* 12(6):555–566 (1986).

Verma et al., Proto–oncogene fos: Complex but versatile regulation, *Cell* 51:513–514 (1987).

Vernallis et al., AChR gene products in chick ciliary ganglia: Transcripts, subunits, and receptors subtypes, *Soc. Neurosci. Abstr.* 17:23 (1991).

Vijayaraghavan et al., Nicotinic receptors that bind α–bungarotoxin on neurons raise intracellular free $Ca^{2+}$, *Neuron* 8:353–362 (1992).

Visvader et al., Two adjacent promotor elements mediate nerve growth factor activation of the c–fos gene and bind distinct nuclear complexes, *Proc. Natl. Acad. Sci. USA* 85:9474–9478 (1988).

Wackym et al., Expression of α4 and β2 nicotinic acetylcholine receptor subunit mRNA and localization of α–bungarotoxin binding proteins in the rat vestibular periphery, *Cell Biology International* 19(4):291–300 (1995).

Wada et al., Functional expression of a new pharmacological subtype of brain nicotinic acetylcholine receptor, *Science* 240:330–334 (1988).

Wada et al., Distribution of Alpha2, Alpha3, Alpha4, and Beta2 neuronal receptor subunit mRNAs in the central nervous system: A hybridization histochemical study in the rat, *J. Comp. Neurol.* 284:314–335 (1989).

Whiting et al., Structurally different neuronal nicotinic acetylcholine receptor subtypes purified and characterized using monoclonal antibodies, *J. Neurosci.* 7(12):4005–4016 (1987).

Whiting et al., Purification and characterization of a nicotinic acetylcholine receptor from rat brain, *Proc. Natl. Acad. Sci. USA* 84:595–599 (1987).

Whiting et al., Affinity labelling of neuronal acetylcholine receptors localizes acetylcholine–binding sites to their β–subunits, *FEBS Lttrs.* 213(1):55–60 (1987).

Whiting et al., Neuronal nicotinic acetylcholine receptor β–subunit is coded for by the cDNA clone $α_4$, *FEBS Lttrs.* 213(1):459–463 (1987).

Whiting et al., Expression of nicotinic acetylcholine receptor subtypes in brain and retina, *Mol. Brain Res.* 10:61–70 (1991).

Whiting et al., Structural and pharmacological characterization of the major brain nicotinic acetylcholine receptor subtype stably expressed in mouse fibroblasts, *Mol. Pharmacol.* 40:463–472 (1991).

Wigler et al., DNA–mediated transfer of the adenine phosphoribosyltransferase locus into mammalian cells, *Proc. Natl. Acad. Sci. USA* 76:1373–1376 (1979).

Williams et al., Neuronal nicotinic actylcholine receptors, *Drug News & Perspectives* 7(4):205–223 (1995).

Willoughby et al., Molecular cloning of a human neuronal nicotinic acetylcholine receptor β3–like subunit, *Neurosci. Lttrs.* 155:136–139 (1993).

Wilson et al., Inhibitory action of nicotinic antagonists on transmitter release at the neuromuscular junction of the rat, *Neurosci. Lttrs.* 186:29–32 (1995).

Yeh et al., Ultrastructural localization of a platelet–derived growth factor/ v–sis–related protein(s) in cytoplasm and nucleus of simian sarcoma virus–transformed cells, *Proc. Natl. Acad. Sci. USA* 84:2317–2321 (1987).

Ymer et al., $GABA_A$ receptor β subunit heterogeneity: functional expression of cloned cDNAs, *EMBO J.* 8:1665–1670 (1989).

Young et al., Isolation and characterization of a new cellular oncogene encoding a protein with multiple potential transmembrane domains, *Cell* 45:711–719 (1986).

Zipser et al., Mapping functional domains in the promoter region of the herpes thymidine kinase gene, *Proc. Natl. Acad. Sci. USA* 78(10):6276–6280 (1981).

Zoli et al., Developmental regulation of nicotinic ACh receptor subunit mRNAs in the rat central and peripheral nervous system, *J. Neurosci.* 15(3):1912–1939 (1995).

Zwart et al., Differential modulation of α3β2 and α3β4 neuronal nicotinic receptors expressed in Xenopus oocytes by flufenamic acid and niflumic acid, *J. Neurosci.* 15(3):2168–2178 (1995).

* cited by examiner

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1743 base pairs
      (B) TYPE: nucleic acid
      (C) STRANDEDNESS: both
      (D) TOPOLOGY: both (ii) MOLECULE TYPE: cDNA (ix) FEATURE:
      (A) NAME/KEY: CDS
      (B) LOCATION: 143..1627
      (D) OTHER INFORMATION: /product= "ALPHA-6 SUBUNIT"

(xi) SEQUENCE DESCRIPTION: SEQ ID NO:1:

```
CGGGTTTTGA TTTCTGAGAA GACACACACG GATTGCAGTG GGCTTCTGAT GATGTCAAGG      60

TTGGATGCAT GTGGCTGACT GATAGCTCTT TGTTTTCCAC AATCCTTTGC CTAGGAAAAA     120

GGAATCCAAG TGTGTTTTAA CC ATG CTG ACC AGC AAG GGG CAG GGA TTC CTT     172
                         Met Leu Thr Ser Lys Gly Gln Gly Phe Leu
                          1               5                  10

CAT GGG GGC TTG TGT CTC TGG CTG TGT GTG TTC ACA CCT TTC TTT AAA     220
His Gly Gly Leu Cys Leu Trp Leu Cys Val Phe Thr Pro Phe Phe Lys
             15                  20                  25

GGC TGT GTG GGC TGT GCA ACT GAG GAG AGG CTC TTC CAC AAA CTG TTT     268
Gly Cys Val Gly Cys Ala Thr Glu Glu Arg Leu Phe His Lys Leu Phe
         30                  35                  40

TCT CAT TAC AAC CAG TTC ATC AGG CCT GTG GAA AAC GTT TCC GAC CCT     316
Ser His Tyr Asn Gln Phe Ile Arg Pro Val Glu Asn Val Ser Asp Pro
     45                  50                  55

GTC ACG GTA CAC TTT GAA GTG GCC ATC ACC CAG CTG GCC AAC GTG GAT     364
Val Thr Val His Phe Glu Val Ala Ile Thr Gln Leu Ala Asn Val Asp
 60                  65                  70

GAA GTA AAC CAG ATC ATG GAA ACC AAT TTG TGG CTG CGT CAC ATC TGG     412
Glu Val Asn Gln Ile Met Glu Thr Asn Leu Trp Leu Arg His Ile Trp
 75                  80                  85                  90

AAT GAT TAT AAA TTG CGC TGG GAT CCA ATG GAA TAT GAT GGC ATT GAG     460
Asn Asp Tyr Lys Leu Arg Trp Asp Pro Met Glu Tyr Asp Gly Ile Glu
             95                 100                 105

ACT CTT CGC GTT CCT GCA GAT AAG ATT TGG AAG CCC GAC ATT GTT CTC     508
Thr Leu Arg Val Pro Ala Asp Lys Ile Trp Lys Pro Asp Ile Val Leu
        110                 115                 120

TAT AAC AAT GCT GTT GGT GAC TTC CAA GTA GAA GGC AAA ACA AAA GCT     556
Tyr Asn Asn Ala Val Gly Asp Phe Gln Val Glu Gly Lys Thr Lys Ala
    125                 130                 135

CTT CTT AAA TAC AAT GGC ATG ATA ACC TGG ACT CCA CCA GCT ATT TTT     604
Leu Leu Lys Tyr Asn Gly Met Ile Thr Trp Thr Pro Pro Ala Ile Phe
    140                 145                 150

AAG AGT TCC TGC CCT ATG GAT ATC ACC TTT TTC CCT TTT GAT CAT CAA     652
Lys Ser Ser Cys Pro Met Asp Ile Thr Phe Phe Pro Phe Asp His Gln
155                 160                 165                 170

AAC TGT TCC CTA AAA TTT GGT TCC TGG ACG TAT GAC AAA GCT GAA ATT     700
Asn Cys Ser Leu Lys Phe Gly Ser Trp Thr Tyr Asp Lys Ala Glu Ile
                175                 180                 185

GAT CTT CTA ATC ATT GGA TCA AAA GTG GAT ATG AAT GAT TTT TGG GAA     748
Asp Leu Leu Ile Ile Gly Ser Lys Val Asp Met Asn Asp Phe Trp Glu
```

```
                   190                195                 200
AAC AGT GAA TGG GAA ATC ATT GAT GCC TCT GGC TAC AAA CAT GAC ATC    796
Asn Ser Glu Trp Glu Ile Ile Asp Ala Ser Gly Tyr Lys His Asp Ile
            205                 210                215

AAA TAC AAC TGT TGT GAA GAG ATA TAC ACA GAT ATA ACC TAT TCT TTC    844
Lys Tyr Asn Cys Cys Glu Glu Ile Tyr Thr Asp Ile Thr Tyr Ser Phe
        220                 225                 230

TAC ATT AGA AGA TTG CCG ATG TTT TAC ACG ATT AAT CTG ATC ATC CCT    892
Tyr Ile Arg Arg Leu Pro Met Phe Tyr Thr Ile Asn Leu Ile Ile Pro
235                 240                 245                 250

TGT CTC TTT ATT TCA TTT CTA ACC GTG TTG GTC TTT TAC CTT CCT TCG    940
Cys Leu Phe Ile Ser Phe Leu Thr Val Leu Val Phe Tyr Leu Pro Ser
                255                 260                 265

GAC TGT GGT GAA AAA GTG ACG CTT TGT ATT TCA GTC CTG CTT TCT CTG    988
Asp Cys Gly Glu Lys Val Thr Leu Cys Ile Ser Val Leu Leu Ser Leu
            270                 275                 280

ACT GTG TTT TTG CTG GTC ATC ACA GAA ACC ATC CCA TCC ACA TCT CTG   1036
Thr Val Phe Leu Leu Val Ile Thr Glu Thr Ile Pro Ser Thr Ser Leu
        285                 290                 295

GTG GTC CCA CTG GTG GGT GAG TAC CTG CTG TTC ACC ATG ATC TTT GTC   1084
Val Val Pro Leu Val Gly Glu Tyr Leu Leu Phe Thr Met Ile Phe Val
300                 305                 310

ACA CTG TCC ATC GTG GTG ACT GTG TTT GTG TTG AAC ATA CAC TAC CGC   1132
Thr Leu Ser Ile Val Val Thr Val Phe Val Leu Asn Ile His Tyr Arg
315                 320                 325                 330

ACC CCA ACC ACG CAC ACA ATG CCC AGG TGG GTG AAG ACA GTT TTC CTG   1180
Thr Pro Thr Thr His Thr Met Pro Arg Trp Val Lys Thr Val Phe Leu
                335                 340                 345

AAG CTG CTG CCC CAG GTC CTG CTG ATG AGG TGG CCT CTG GAC AAG ACA   1228
Lys Leu Leu Pro Gln Val Leu Leu Met Arg Trp Pro Leu Asp Lys Thr
            350                 355                 360

AGG GGC ACA GGC TCT GAT GCA GTG CCC AGA GGC TTG GCC AGG AGG CCT   1276
Arg Gly Thr Gly Ser Asp Ala Val Pro Arg Gly Leu Ala Arg Arg Pro
        365                 370                 375

GCC AAA GGC AAG CTT GCA AGC CAT GGG GAA CCC AGA CAT CTT AAA GAA   1324
Ala Lys Gly Lys Leu Ala Ser His Gly Glu Pro Arg His Leu Lys Glu
380                 385                 390

TGC TTC CAT TGT CAC AAA TCA AAT GAG CTT GCC ACA AGC AAG AGA AGA   1372
Cys Phe His Cys His Lys Ser Asn Glu Leu Ala Thr Ser Lys Arg Arg
395                 400                 405                 410

TTA AGT CAT CAG CCA TTA CAG TGG GTG GTG GAA AAT TCG GAG CAC TCG   1420
Leu Ser His Gln Pro Leu Gln Trp Val Val Glu Asn Ser Glu His Ser
                415                 420                 425

CCT GAA GTT GAA GAT GTG ATT AAC AGT GTT CAG TTC ATA GCA GAA AAC   1468
Pro Glu Val Glu Asp Val Ile Asn Ser Val Gln Phe Ile Ala Glu Asn
            430                 435                 440

ATG AAG AGC CAC AAT GAA ACC AAG GAG GTA GAA GAT GAC TGG AAA TAC   1516
Met Lys Ser His Asn Glu Thr Lys Glu Val Glu Asp Asp Trp Lys Tyr
        445                 450                 455

GTG GCC ATG GTG GTG GAC AGA GTA TTT CTT TGG GTA TTT ATA ATT GTC   1564
Val Ala Met Val Val Asp Arg Val Phe Leu Trp Val Phe Ile Ile Val
460                 465                 470

TGT GTA TTT GGA ACT GCA GGG CTA TTT CTA CAG CCA CTA CTT GGG AAC   1612
Cys Val Phe Gly Thr Ala Gly Leu Phe Leu Gln Pro Leu Leu Gly Asn
475                 480                 485                 490

ACA GGA AAA TCT TAAAATGTAT TTTCTTTTAT GTTCAGAAAT TTACAGACAC       1664
Thr Gly Lys Ser
            495

CATATTTGTT CTGCATTCCC TGCCACAAGG AAAGGAAAGC AAAGGCTTCC CACCCAAGTC 1724
```

CCCCATCTGC TAAAACCCG                                                                                    1743

(2) INFORMATION FOR SEQ ID NO:2:

(i) SEQUENCE CHARACTERISTICS:
       (A) LENGTH: 494 amino acids
       (B) TYPE: amino acid
       (D) TOPOLOGY: linear (ii) MOLECULE TYPE: protein (xi) SEQUENCE DESCRIPTION: SEQ ID NO:2:

Met Leu Thr Ser Lys Gly Gln Gly Phe Leu His Gly Gly Leu Cys Leu
  1               5                  10                  15

Trp Leu Cys Val Phe Thr Pro Phe Lys Gly Cys Val Gly Cys Ala
                 20                  25                  30

Thr Glu Glu Arg Leu Phe His Lys Leu Phe Ser His Tyr Asn Gln Phe
                 35                  40                  45

Ile Arg Pro Val Glu Asn Val Ser Asp Pro Val Thr Val His Phe Glu
         50                  55                  60

Val Ala Ile Thr Gln Leu Ala Asn Val Asp Glu Val Asn Gln Ile Met
 65                  70                  75                  80

Glu Thr Asn Leu Trp Leu Arg His Ile Trp Asn Asp Tyr Lys Leu Arg
                 85                  90                  95

Trp Asp Pro Met Glu Tyr Asp Gly Ile Glu Thr Leu Arg Val Pro Ala
                100                 105                 110

Asp Lys Ile Trp Lys Pro Asp Ile Val Leu Tyr Asn Asn Ala Val Gly
                115                 120                 125

Asp Phe Gln Val Glu Gly Lys Thr Lys Ala Leu Leu Lys Tyr Asn Gly
        130                 135                 140

Met Ile Thr Trp Thr Pro Pro Ala Ile Phe Lys Ser Ser Cys Pro Met
145                 150                 155                 160

Asp Ile Thr Phe Phe Pro Phe Asp His Gln Asn Cys Ser Leu Lys Phe
                165                 170                 175

Gly Ser Trp Thr Tyr Asp Lys Ala Glu Ile Asp Leu Leu Ile Ile Gly
                180                 185                 190

Ser Lys Val Asp Met Asn Asp Phe Trp Glu Asn Ser Glu Trp Glu Ile
            195                 200                 205

Ile Asp Ala Ser Gly Tyr Lys His Asp Ile Lys Tyr Asn Cys Cys Glu
        210                 215                 220

Glu Ile Tyr Thr Asp Ile Thr Tyr Ser Phe Tyr Ile Arg Arg Leu Pro
225                 230                 235                 240

Met Phe Tyr Thr Ile Asn Leu Ile Ile Pro Cys Leu Phe Ile Ser Phe
                245                 250                 255

Leu Thr Val Leu Val Phe Tyr Leu Pro Ser Asp Cys Gly Glu Lys Val
                260                 265                 270

Thr Leu Cys Ile Ser Val Leu Leu Ser Leu Thr Val Phe Leu Leu Val
            275                 280                 285

Ile Thr Glu Thr Ile Pro Ser Thr Ser Leu Val Val Pro Leu Val Gly
        290                 295                 300

Glu Tyr Leu Leu Phe Thr Met Ile Phe Val Thr Leu Ser Ile Val Val
305                 310                 315                 320

Thr Val Phe Val Leu Asn Ile His Tyr Arg Thr Pro Thr Thr His Thr
                325                 330                 335

Met Pro Arg Trp Val Lys Thr Val Phe Leu Lys Leu Leu Pro Gln Val

-continued

```
                    340              345                350
Leu Leu Met Arg Trp Pro Leu Asp Lys Thr Arg Gly Thr Gly Ser Asp
            355              360              365

Ala Val Pro Arg Gly Leu Ala Arg Arg Pro Ala Lys Gly Lys Leu Ala
    370              375              380

Ser His Gly Glu Pro Arg His Leu Lys Glu Cys Phe His Cys His Lys
385              390              395              400

Ser Asn Glu Leu Ala Thr Ser Lys Arg Arg Leu Ser His Gln Pro Leu
                405              410              415

Gln Trp Val Val Glu Asn Ser Glu His Ser Pro Glu Val Glu Asp Val
            420              425              430

Ile Asn Ser Val Gln Phe Ile Ala Glu Asn Met Lys Ser His Asn Glu
            435              440              445

Thr Lys Glu Val Glu Asp Asp Trp Lys Tyr Val Ala Met Val Val Asp
    450              455              460

Arg Val Phe Leu Trp Val Phe Ile Ile Val Cys Val Phe Gly Thr Ala
465              470              475              480

Gly Leu Phe Leu Gln Pro Leu Leu Gly Asn Thr Gly Lys Ser
                485              490
```

(2) INFORMATION FOR SEQ ID NO:3:

(i) SEQUENCE CHARACTERISTICS:
        (A) LENGTH: 1927 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 98..1474
        (D) OTHER INFORMATION: /product= "BETA-3 SUBUNIT"

(xi) SEQUENCE DESCRIPTION: SEQ ID NO:3:

```
TCGGAACCCC TGTATTTTCT TTTCAAAACC CCCTTTTCCA GTGGAAATGC TCTGTTGTTA      60

AAAAGGAAGA AACTGTCTTT CTGAAACTGA CATCACG ATG CTC CCA GAT TTT ATG     115
                                        Met Leu Pro Asp Phe Met
                                          1               5

CTG GTT CTC ATC GTC CTT GGC ATC CCT TCC TCA GCC ACC ACA GGT TTC     163
Leu Val Leu Ile Val Leu Gly Ile Pro Ser Ser Ala Thr Thr Gly Phe
            10              15              20

AAC TCA ATC GCC GAA AAT GAA GAT GCC CTC CTC AGA CAT TTG TTC CAA     211
Asn Ser Ile Ala Glu Asn Glu Asp Ala Leu Leu Arg His Leu Phe Gln
        25              30              35

GGT TAT CAG AAA TGG GTC CGC CCT GTA TTA CAT TCT AAT GAC ACC ATA     259
Gly Tyr Gln Lys Trp Val Arg Pro Val Leu His Ser Asn Asp Thr Ile
    40              45              50

AAA GTA TAT TTT GGA TTG AAA ATA TCC CAG CTT GTA GAT GTG GAT GAA     307
Lys Val Tyr Phe Gly Leu Lys Ile Ser Gln Leu Val Asp Val Asp Glu
55              60              65              70

AAG AAT CAG CTG ATG ACA ACC AAT GTG TGG CTC AAA CAG GAA TGG ACA     355
Lys Asn Gln Leu Met Thr Thr Asn Val Trp Leu Lys Gln Glu Trp Thr
            75              80              85

GAC CAC AAG TTA CGC TGG AAT CCT GAT GAT TAT GGT GGG ATC CAT TCC     403
Asp His Lys Leu Arg Trp Asn Pro Asp Asp Tyr Gly Gly Ile His Ser
        90              95              100

ATT AAA GTT CCA TCA GAA TCT CTG TGG CTT CCT GAC ATA GTT CTC TTT     451
Ile Lys Val Pro Ser Glu Ser Leu Trp Leu Pro Asp Ile Val Leu Phe
```

```
              105                 110                 115
GAA AAT GCT GAC GGC CGC TTC GAA GGC TCC CTG ATG ACC AAG GTC ATC      499
Glu Asn Ala Asp Gly Arg Phe Glu Gly Ser Leu Met Thr Lys Val Ile
    120                 125                 130

GTG AAA TCA AAC GGA ACT GTT GTC TGG ACC CCT CCC GCC AGC TAC AAA      547
Val Lys Ser Asn Gly Thr Val Val Trp Thr Pro Pro Ala Ser Tyr Lys
135                 140                 145                 150

AGC TCC TGC ACC ATG GAC GTC ACG TTT TTC CCG TTC GAC CGA CAG AAC      595
Ser Ser Cys Thr Met Asp Val Thr Phe Phe Pro Phe Asp Arg Gln Asn
                155                 160                 165

TGC TCC ATG AAG TTT GGA TCC TGG ACT TAT GAT GGC ACC ATG GTT GAC      643
Cys Ser Met Lys Phe Gly Ser Trp Thr Tyr Asp Gly Thr Met Val Asp
            170                 175                 180

CTC ATT TTG ATC AAT GAA AAT GTC GAC AGA AAA GAC TTC TTC GAT AAC      691
Leu Ile Leu Ile Asn Glu Asn Val Asp Arg Lys Asp Phe Phe Asp Asn
        185                 190                 195

GGA GAA TGG GAA ATA CTG AAT GCA AAG GGG ATG AAG GGG AAC AGA AGG      739
Gly Glu Trp Glu Ile Leu Asn Ala Lys Gly Met Lys Gly Asn Arg Arg
    200                 205                 210

GAC GGC GTG TAC TCC TAT CCC TTT ATC ACG TAT TCC TTC GTC CTG AGA      787
Asp Gly Val Tyr Ser Tyr Pro Phe Ile Thr Tyr Ser Phe Val Leu Arg
215                 220                 225                 230

CGC CTG CCT TTA TTC TAT ACC CTC TTT CTC ATC ATC CCC TGC CTG GGG      835
Arg Leu Pro Leu Phe Tyr Thr Leu Phe Leu Ile Ile Pro Cys Leu Gly
                235                 240                 245

CTG TCT TTC CTA ACA GTT CTT GTG TTC TAT TTA CCT TCG GAT GAA GGA      883
Leu Ser Phe Leu Thr Val Leu Val Phe Tyr Leu Pro Ser Asp Glu Gly
            250                 255                 260

GAA AAA CTT TCA TTA TCC ACA TCG GTC TTG GTT TCT CTG ACA GTT TTC      931
Glu Lys Leu Ser Leu Ser Thr Ser Val Leu Val Ser Leu Thr Val Phe
        265                 270                 275

CTT TTA GTG ATT GAA GAA ATC ATC CCA TCG TCT TCC AAA GTC ATT CCT      979
Leu Leu Val Ile Glu Glu Ile Ile Pro Ser Ser Ser Lys Val Ile Pro
    280                 285                 290

CTC ATT GGA GAG TAC CTG CTG TTC ATC ATG ATT TTT GTG ACC CTG TCC     1027
Leu Ile Gly Glu Tyr Leu Leu Phe Ile Met Ile Phe Val Thr Leu Ser
295                 300                 305                 310

ATC ATT GTT ACC GTG TTT GTC ATT AAC GTT CAC CAC AGA TCT TCT TCC     1075
Ile Ile Val Thr Val Phe Val Ile Asn Val His His Arg Ser Ser Ser
                315                 320                 325

ACG TAC CAC CCC ATG GCC CCC TGG GTT AAG AGG CTC TTT CTG CAG AAA     1123
Thr Tyr His Pro Met Ala Pro Trp Val Lys Arg Leu Phe Leu Gln Lys
            330                 335                 340

CTT CCA AAA TTA CTT TGC ATG AAA GAT CAT GTG GAT CGC TAC TCA TCC     1171
Leu Pro Lys Leu Leu Cys Met Lys Asp His Val Asp Arg Tyr Ser Ser
        345                 350                 355

CCA GAG AAA GAG GAG AGT CAA CCA GTA GTG AAA GGC AAA GTC CTC GAA     1219
Pro Glu Lys Glu Glu Ser Gln Pro Val Val Lys Gly Lys Val Leu Glu
    360                 365                 370

AAA AAG AAA CAG AAA CAG CTT AGT GAT GGA GAA AAA GTT CTA GTT GCT     1267
Lys Lys Lys Gln Lys Gln Leu Ser Asp Gly Glu Lys Val Leu Val Ala
375                 380                 385                 390

TTT TTG GAA AAA GCT GCT GAT TCC ATT AGA TAC ATT TCC AGA CAT GTG     1315
Phe Leu Glu Lys Ala Ala Asp Ser Ile Arg Tyr Ile Ser Arg His Val
                395                 400                 405

AAG AAA GAA CAT TTT ATC AGC CAG GTA GTA CAA GAC TGG AAA TTT GTA     1363
Lys Lys Glu His Phe Ile Ser Gln Val Val Gln Asp Trp Lys Phe Val
            410                 415                 420

GCT CAA GTT CTT GAC CGA ATC TTC CTG TGG CTC TTT CTG ATA GTG TCA     1411
```

-continued

```
Ala Gln Val Leu Asp Arg Ile Phe Leu Trp Leu Phe Leu Ile Val Ser
            425                 430                 435
GCA ACA GGC TCG GTT CTG ATT TTT ACC CCT GCT TTG AAG ATG TGG CTA      1459
Ala Thr Gly Ser Val Leu Ile Phe Thr Pro Ala Leu Lys Met Trp Leu
        440                 445                 450
CAT AGT TAC CAT TAGGAATTTC AAAAGACATA AGTACTAAAT TACACCTTAG          1511
His Ser Tyr His
455

ACCTGACATC TGGCTATCAC ACAGACAGAA TCCAAATGCA TGTGCTTGTT CTACGAACCC    1571
CGAATGCGTT GTCTTTGTGG AAATGGAACA TCTCCTCATG GGAGAAACTC TGGTAAATGT    1631
GCTCATTTGT GGTTGCCATG AGAGTGAGCT GCTTTTAAAG AAAGTGGAGC CTCCTCAGAC    1691
CCCTGCCTTG GCTTTCCCAG ACATTCAGGG AGGGATCATA GGTCCAGGCT TGAGCTCACA    1751
TGTGGCCAGA GTGCACAAAA AGCTGTTGCT ACTTGGTGGA GGAACACCTC CTAGAAGCAG    1811
CAGGCCTCGG TGGTGGGGGA GGGGGGATTC ACCTGGAATT AAGGAAGTCT CGGTGTCGAG    1871
CTATCTGTGT GGGCAGAGCC TGGATCTCCC ACCCTGCACT GGCCTCCTTG GTGCCG        1927

(2) INFORMATION FOR SEQ ID NO:4:

(i) SEQUENCE CHARACTERISTICS:
        (A) LENGTH: 458 amino acids
        (B) TYPE: amino acid
        (D) TOPOLOGY: linear (ii) MOLECULE TYPE: protein (xi) SEQUENCE DESCRIPTION: SEQ ID NO:4:

Met Leu Pro Asp Phe Met Leu Val Leu Ile Val Leu Gly Ile Pro Ser
  1               5                  10                  15

Ser Ala Thr Thr Gly Phe Asn Ser Ile Ala Glu Asn Glu Asp Ala Leu
             20                  25                  30

Leu Arg His Leu Phe Gln Gly Tyr Gln Lys Trp Val Arg Pro Val Leu
         35                  40                  45

His Ser Asn Asp Thr Ile Lys Val Tyr Phe Gly Leu Lys Ile Ser Gln
     50                  55                  60

Leu Val Asp Val Asp Glu Lys Asn Gln Leu Met Thr Thr Asn Val Trp
 65                  70                  75                  80

Leu Lys Gln Glu Trp Thr Asp His Lys Leu Arg Trp Asn Pro Asp Asp
                 85                  90                  95

Tyr Gly Gly Ile His Ser Ile Lys Val Pro Ser Glu Ser Leu Trp Leu
            100                 105                 110

Pro Asp Ile Val Leu Phe Glu Asn Ala Asp Gly Arg Phe Glu Gly Ser
        115                 120                 125

Leu Met Thr Lys Val Ile Val Lys Ser Asn Gly Thr Val Val Trp Thr
    130                 135                 140

Pro Pro Ala Ser Tyr Lys Ser Ser Cys Thr Met Asp Val Thr Phe Phe
145                 150                 155                 160

Pro Phe Asp Arg Gln Asn Cys Ser Met Lys Phe Gly Ser Trp Thr Tyr
                165                 170                 175

Asp Gly Thr Met Val Asp Leu Ile Leu Ile Asn Glu Asn Val Asp Arg
            180                 185                 190

Lys Asp Phe Phe Asp Asn Gly Glu Trp Glu Ile Leu Asn Ala Lys Gly
        195                 200                 205

Met Lys Gly Asn Arg Arg Asp Gly Val Tyr Ser Tyr Pro Phe Ile Thr
    210                 215                 220
```

―continued

```
Tyr Ser Phe Val Leu Arg Arg Leu Pro Leu Phe Tyr Thr Leu Phe Leu
225                 230             235             240

Ile Ile Pro Cys Leu Gly Leu Ser Phe Leu Thr Val Leu Val Phe Tyr
            245             250             255

Leu Pro Ser Asp Glu Gly Glu Lys Leu Ser Leu Ser Thr Ser Val Leu
            260             265             270

Val Ser Leu Thr Val Phe Leu Leu Val Ile Glu Glu Ile Ile Pro Ser
        275             280             285

Ser Ser Lys Val Ile Pro Leu Ile Gly Glu Tyr Leu Leu Phe Ile Met
        290             295             300

Ile Phe Val Thr Leu Ser Ile Ile Val Thr Val Phe Val Ile Asn Val
305             310             315             320

His His Arg Ser Ser Ser Thr Tyr His Pro Met Ala Pro Trp Val Lys
            325             330             335

Arg Leu Phe Leu Gln Lys Leu Pro Lys Leu Leu Cys Met Lys Asp His
            340             345             350

Val Asp Arg Tyr Ser Ser Pro Glu Lys Glu Glu Ser Gln Pro Val Val
            355             360             365

Lys Gly Lys Val Leu Glu Lys Lys Gln Lys Gln Leu Ser Asp Gly
370             375             380

Glu Lys Val Leu Val Ala Phe Leu Glu Lys Ala Ala Asp Ser Ile Arg
385             390             395             400

Tyr Ile Ser Arg His Val Lys Lys Glu His Phe Ile Ser Gln Val Val
            405             410             415

Gln Asp Trp Lys Phe Val Ala Gln Val Leu Asp Arg Ile Phe Leu Trp
            420             425             430

Leu Phe Leu Ile Val Ser Ala Thr Gly Ser Val Leu Ile Phe Thr Pro
        435             440             445

Ala Leu Lys Met Trp Leu His Ser Tyr His
    450             455
```

HUMAN NEURONAL NICOTINIC ACETYLCHOLINE RECEPTOR α6 AND β3 NUCLEIC ACID

This invention relates to DNA encoding human neuronal nicotinic acetylcholine receptor protein subunits, as well as the proteins themselves. In particular, human neuronal nicotinic acetylcholine receptor α-subunit-encoding DNA, α-subunit proteins, β-subunit-encoding DNA, β-subunit proteins, and combinations thereof are provided.

BACKGROUND OF THE INVENTION

Ligand-gated ion channels provide a means for communication between cells of the central nervous system. These channels convert a signal (e.g., a chemical referred to as a neurotransmitter) that is released by one cell into an electrical signal that propagates along a target cell membrane. A variety of neurotransmitters and neurotransmitter receptors exist in the central and peripheral nervous systems. Five families of ligand-gated receptors, including the nicotinic acetylcholine receptors (nAChRs) of neuromuscular and neuronal origins, have been identified (Stroud et al. (1990) Biochemistry 29:11009–11023). There is, however, little understanding of the manner in which the variety of receptors generates different responses to neurotransmitters or to other modulating ligands in different regions of the nervous system.

The nicotinic acetylcholine receptors (nAChRs) are multisubunit proteins of neuromuscular and neuronal origins. These receptors form ligand-gated ion channels that mediate synaptic transmission between nerve and muscle and between neurons upon interaction with the neurotransmitter acetylcholine (ACh). Since various neuronal nicotinic acetylcholine receptor (nAChR) subunits exist, a variety of nAChR compositions (i.e., combinations of subunits) exist. The different nAChR compositions exhibit different specificities for various ligands and are thereby pharmacologically distinguishable. Thus, the nicotinic acetylcholine receptors expressed at the vertebrate neuromuscular junction, in vertebrate sympathetic ganglia and in the vertebrate central nervous system have been distinguished on the basis of the effects of various ligands that bind to different nAChR compositions. For example, the elapid α-neurotoxins that block activation of nicotinic acetylcholine receptors at the neuromuscular junction do not block activation of some neuronal nicotinic acetylcholine receptors that are expressed on several different neuron-derived cell lines.

Muscle nAChR is a glycoprotein composed of five subunits with the stoichiometry $(\alpha)_2\beta(\gamma$ or $\epsilon)$ $\delta$. Each of the subunits has a mass of about 50–60 kilodaltons (kd) and is encoded by a different gene. The $(\alpha)_2\beta(\gamma$ or $\epsilon)$ $\delta$ complex forms functional receptors containing two ligand binding sites and a ligand-gated transmembrane channel. Upon interaction with a cholinergic agonist, muscle nicotinic nAChRs conduct sodium ions. The influx of sodium ions rapidly short-circuits the normal ionic gradient maintained across the plasma membrane, thereby depolarizing the membrane. By reducing the potential difference across the membrane, a chemical signal is transduced into an electrical signal at the neuromuscular junction that induces muscle contraction.

Functional muscle nicotinic acetylcholine receptors have been formed with αβδγ subunits, αβγ subunits, αβδ add subunits, αβγ subunits or αδ subunits, but not with only one subunit (see e.g., Kurosaki et al. (1987) FEBS Lett. 214: 253–258; Camacho et al. (1993) J. Neuroscience 13:605–613). In contrast, functional neuronal nAChRs can be formed from a subunits alone or combinations of α and β subunits. The larger a subunit is generally believed to be a ACh-binding subunit and the lower molecular weight β subunit is generally believed to be the structural subunit, although it has not been definitively demonstrated that the a subunit does not have the ability to bind ACh or participate in the formation of the ACh binding site. Each of the subunits which participate in the formation of a functional ion channel are, to the extent they contribute to the structure of the resulting channel, "structural" subunits, regardless of their ability (or inability) to bind ACh. Neuronal nAChRs, which are also ligand-gated ion channels, are expressed in ganglia of the autonomic nervous system and in the central nervous system (where they mediate signal transmission), in post-synaptic locations (where they modulate transmission), and in pre- and extra-synaptic locations (where they modulate neurotransmission and may have additional functions; Wonnacott et al., In: Progress in Brain Research (A. Nordberg et al., (Eds) Elsevier, Amsterdam) 157–163 (1990)).

DNA encoding nAChRs has been isolated from several sources. Based on the information available from such work, it has been evident for some time that nAChRs expressed in muscle, in autonomic ganglia, and in the central nervous system are functionally diverse. This functional diversity could be due, at least in part, to the large number of different nAChR subunits which exist. There is an incomplete understanding, however, of how (and which) nAChR subunits combine to generate unique nAChR subtypes, particularly in neuronal cells. Indeed, there is evidence that only certain nAChR subtypes may be involved in diseases such as Alzheimer's disease. Moreover, it is not clear whether nAChRs from analogous tissues or cell types are similar across species.

Accordingly, there is a need for the isolation characterization of DNAs encoding each human neuronal nAChR subunit, recombinant cells containing such subunits and receptors prepared therefrom. In order to study the function of human neuronal nAChRs and to obtain disease-specific pharmacologically active agents, there is also a need to obtain isolated (preferably purified) human neuronal nAChRs, and isolated (preferably purified) human neuronal nAChR subunits. In addition, there is also a need to develop assays to identify such pharmacologically active agents.

The availability of such DNAs, cells, receptor subunits and receptor compositions will eliminate the uncertainty of speculating as to human neuronal nAChR structure and function based on predictions drawn from non-human nAChR data, or human or non-human muscle or ganglia nAChR data.

Therefore, it is an object herein to isolate and characterize DNA encoding subunits of human neuronal nicotinic acetylcholine receptors. It is also an object herein to provide methods for recombinant production of human neuronal nicotinic acetylcholine receptor subunits. It is also an object herein to provide purified receptor subunits and to provide methods for screening compounds to identify compounds that modulate the activity of human neuronal nAChRs.

These and other objects will become apparent to those of skill in the art upon further study of the specification and claims.

BRIEF DESCRIPTION OF THE INVENTION

In accordance with the present invention, there are provided isolated DNAs encoding novel human alpha and beta subunits of neuronal nAChRs. In particular, isolated DNA encoding human $\alpha_6$ and $\beta_3$ subunits of neuronal nAChRs are provided. Messenger RNA and polypeptides encoded by the above-described DNA are also provided.

Further in accordance with the present invention, there are provided recombinant human neuronal nicotinic nAChR subunits, including $\alpha_6$ and $\beta_3$ subunits, as well as methods for the production thereof. In addition, recombinant human neuronal nicotinic acetylcholine receptors containing at least one human neuronal nicotinic nAChR subunit are also provided, as well as methods for the production thereof. Further provided are recombinant neuronal nicotinic nAChRs that contain a mixture of one or more nAChR subunits encoded by a host cell, and one or more nAChR subunits encoded by heterologous DNA or RNA (i.e., DNA or RNA as described herein that has been introduced into the host cell), as well as methods for the production thereof.

Plasmids containing DNA encoding the above-described subunits are also provided. Recombinant cells containing the above-described DNA, mRNA or plasmids are also provided herein. Such cells are useful, for example, for replicating DNA, for producing human nAChR subunits and recombinant receptors, and for producing cells that express receptors containing one or more human subunits.

The DNA, mRNA, vectors, receptor subunits, receptor subunit combinations and cells provided herein permit production of selected neuronal nicotinic nAChR receptor subtypes and specific combinations thereof, as well as antibodies to said receptor subunits. This provides a means to prepare synthetic or recombinant receptors and receptor subunits that are substantially free of contamination from many other receptor proteins whose presence can interfere with analysis of a single nAChR subtype. The availability of desired receptor subtypes makes it possible to observe the effect of a drug substance on a particular receptor subtype and to thereby perform initial in vitro screening of the drug substance in a test system that is specific for humans and specific for a human neuronal nicotinic nAChR subtype.

The ability to screen drug substances in vitro to determine the effect of the drug on specific receptor compositions should permit the development and screening of receptor subtype-specific or disease-specific drugs. Also, testing of single receptor subunits or specific receptor subtype combinations with a variety of potential agonists or antagonists provides additional information with respect to the function and activity of the individual subunits and should lead to the identification and design of compounds that are capable of very specific interaction with one or more of the receptor subunits or receptor subtypes. The resulting drugs should exhibit fewer unwanted side effects than drugs identified by screening with cells that express a variety of subtypes.

Further in relation to drug development and therapeutic treatment of various disease states, the availability of DNAs encoding human neuronal nAChR subunits enables identification of any alterations in such genes (e.g., mutations) which may correlate with the occurrence of certain disease states. In addition, the creation of animal models of such disease states becomes possible, by specifically introducing such mutations into synthetic DNA sequences which can then be introduced into laboratory animals or in vitro assay systems to determine the effects thereof.

DETAILED DESCRIPTION OF THE INVENTION

Figure 1:
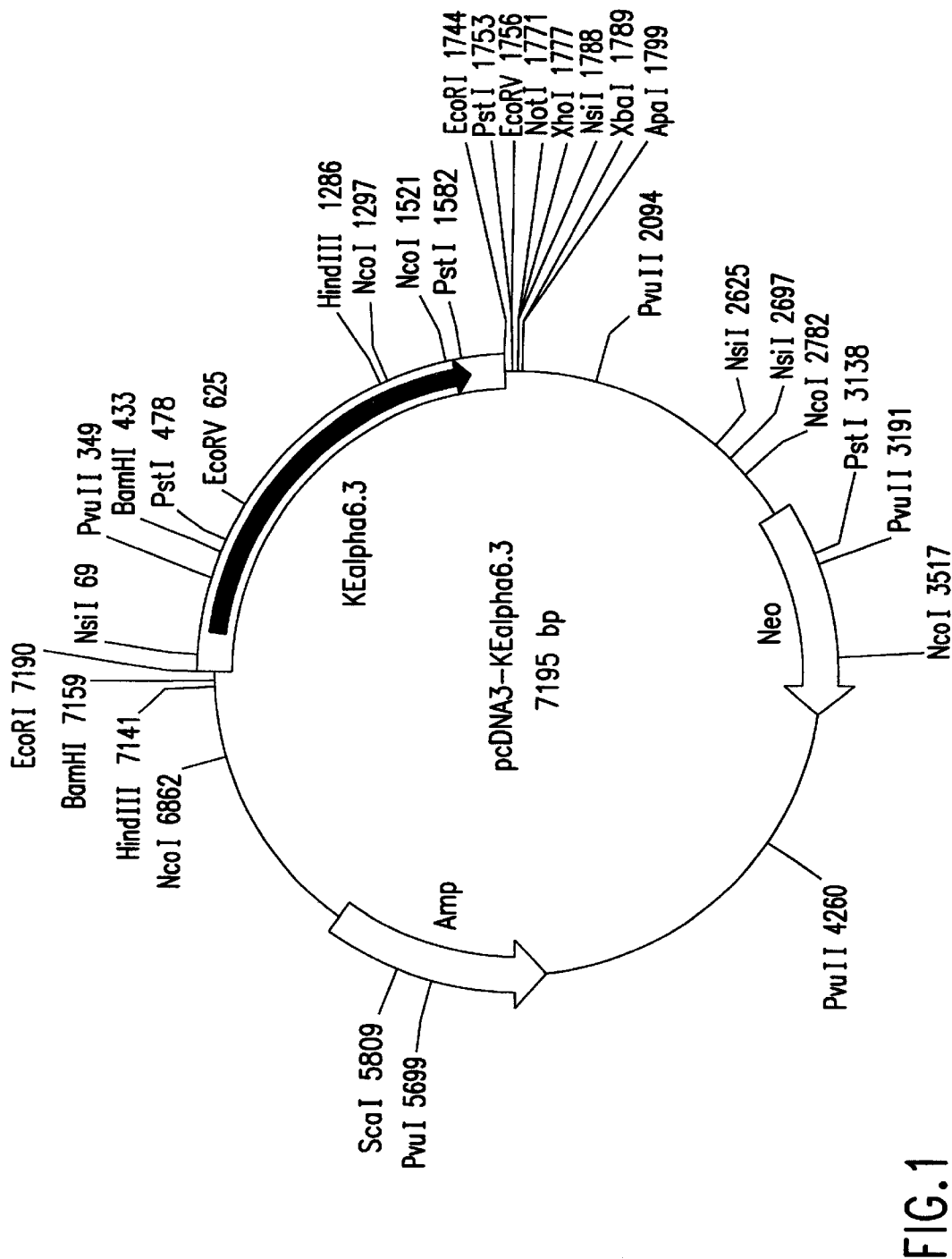
FIG. 1 presents a restriction map of a cytomegalovirus (CMV) promoter-based vector, pcDNA3-KEalpha6.3, which contains an $\alpha_6$-encoding sequence as an EcoRI insert.

In accordance with the present invention, we have isolated and characterized DNAs encoding novel human alpha and beta subunits of neuronal nAChRs. Specifically, isolated DNAs encoding human $\alpha_6$ and $\beta_3$ subunits of neuronal nAChRs are described herein. Recombinant messenger RNA (mRNA) and recombinant polypeptides encoded by the above-described DNA are also provided.

As used herein, isolated (or substantially pure) as a modifier of DNA, RNA, polypeptides or proteins means that the DNA, RNA, polypeptides or proteins so designated have been separated from their in vivo cellular environments through the efforts of human beings. Thus as used herein, isolated (or substantially pure) DNA refers to DNAs purified according to standard techniques employed by those skilled in the art (see, e.g., Sambrook et al. (1989) *Molecular Cloning: A Laboratory Manual*, 2nd ed., Cold Spring Harbor Laboratory Press, Cold Spring Harbor, N.Y.).

Similarly, as used herein, "recombinant" as a modifier of DNA, RNA, polypeptides or proteins means that the DNA, RNA, polypeptides or proteins so designated have been prepared by the efforts of human beings, e.g., by cloning, recombinant expression, and the like. Thus as used herein, recombinant proteins, for example, refers to proteins produced by a recombinant host, expressing DNAs which have been added to that host through the efforts of human beings.

As used herein, a human alpha subunit gene is a gene that encodes an alpha subunit of a human neuronal nicotinic acetylcholine receptor. The alpha subunit is a subunit of the nAChR to which ACh binds. Assignment of the name "alpha" to a putative nAChR subunit, according to Deneris et al. [Tips (1991) 12:34–40] is based on the conservation of adjacent cysteine residues in the presumed extracellular domain of the subunit that are the homologues of cysteines 192 and 193 of the Torpedo alpha subunit (see Noda et al. (1982) Nature 299:793–797). As used herein, an alpha subunit subtype refers to a human neuronal nAChR subunit that is encoded by DNA that hybridizes under high stringency conditions to at least one of the neuronal nAChR alpha subunit-encoding DNAs (or deposited clones) disclosed herein. An alpha subunit generally binds to ACh under physiological conditions and at physiological concentrations and, in the optional presence of a beta subunit (i.e., some alpha subunits are functional alone, while others require the presence of a beta subunit), generally forms a functional nAChR as assessed by methods described herein or known to those of skill in this art.

Also contemplated are alpha subunits encoded by DNAs that encode alpha subunits as defined above, but that by virtue of degeneracy of the genetic code do not necessarily hybridize to the disclosed DNA or deposited clones under specified hybridization conditions. Such subunits also form a functional receptor, as assessed by the methods described herein or known to those of skill in the art, generally with one or more beta subunit subtypes. Typically, unless an alpha subunit is encoded by RNA that arises from alternative splicing (i.e., a splice variant), alpha-encoding DNA and the alpha subunit encoded thereby share substantial sequence homology with at least one of the alpha subunit DNAs (and proteins encoded thereby) described or deposited herein. It is understood that DNA or RNA encoding a splice variant may overall share less than 90% homology with the DNA or RNA provided herein, but include regions of nearly 100% homology to a DNA fragment or deposited clone described herein, and encode an open reading frame that includes start and stop codons and encodes a functional alpha subunit.

As used herein, a splice variant refers to variant nAChR subunit-encoding nucleic acid(s) produced by differential processing of primary transcript(s) of genomic DNA, resulting in the production of more than one type of mRNA. cDNA derived from differentially processed genomic DNA will encode nAChR subunits that have regions of complete amino acid identity and regions having different amino acid sequences. Thus, the same genomic sequence can lead to the production of multiple, related mRNAs and proteins. Both the resulting mRNAs and proteins are referred to herein as "splice variants".

Stringency of hybridization is used herein to refer to conditions under which polynucleic acid hybrids are stable. As known to those of skill in the art, the stability of hybrids is reflected in the melting temperature ($T_m$) of the hybrids. $T_m$ can be approximated by the formula:

$$81.5° C. -16.6(\log_{10}[Na^+]) + 0.41(\%G+C) - 600/1,$$

where 1 is the length of the hybrids in nucleotides. $T_m$ decreases approximately 1–1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions. Thus, as used herein:

(1) HIGH STRINGENCY conditions, with respect to fragment hybridization, refer to conditions that permit hybridization of only those nucleic acid sequences that form stable hybrids in 0.018M NaCl at 650° C. (i.e., if a hybrid is not stable in 0.018M NaCl at 65° C., it will not be stable under high stringency conditions, as contemplated herein). High stringency conditions can be provided, for example, by hybridization in 50% formamide, 5×Denhardt's solution, 5×SSPE, 0.2% SDS, 200 µg/ml denatured sonicated herring sperm DNA, at 42° C., followed by washing in 0.1×SSPE, and 0.1% SDS at 65° C.;

(2) MODERATE STRINGENCY conditions, with respect to fragment hybridization, refer to conditions equivalent to hybridization in 50% formamide, 5×Denhardt's solution, 5×SSPE, 0.2% SDS, 200 µg/ml denatured sonicated herring sperm DNA, at 42° C., followed by washing in 0.2×SSPE, 0.2% SDS, at 60° C.;

(3) LOW STRINGENCY conditions, with respect to fragment hybridization, refer to conditions equivalent to hybridization in 10% formamide, 5×Denhardt's solution, 6×SSPE, 0.2% SDS, 200 µg/ml denatured sonicated herring sperm DNA, followed by washing in 1×SSPE, 0.2% SDS, at 50° C.; and (4) HIGH STRINGENCY conditions, with respect to oligonucleotide (i.e., synthetic DNA≦about 30 nucleotides in length) hybridization, refer to conditions equivalent to hybridization in 10% formamide, 5×Denhardt's solution, 6×SSPE, 0.2% SDS, 200 µg/ml denatured sonicated herring sperm DNA, at 42° C., followed by washing in 1×SSPE, and 0.2% SDS at 50° C.

It is understood that these conditions may be duplicated using a variety of buffers and temperatures and that they are not necessarily precise.

Denhardt's solution and SSPE (see, e.g., Sambrook et al., supra) are well known to those of skill in the art as are other suitable hybridization buffers. For example, SSPE is pH 7.4 phosphate-buffered 0.18M NaCl. SSPE can be prepared, for example, as a 20× stock solution by dissolving 175.3 g of NaCl, 27.6 g of $NaH_2PO_4$ and 7.4 g EDTA in 800 ml of water, adjusting the pH to 7.4, and then adding water to 1 liter. Denhardt's solution (see, Denhardt (1966) Biochem. Biophys. Res. Commun. 23:641) can be prepared, for example, as a 50× stock solution by mixing 5 g Ficoll (Type 400, Pharmacia LKB Biotechnology, INC., Piscataway N.J.), 5 g of polyvinylpyrrolidone, 5 g bovine serum albumin (Fraction V; Sigma, St. Louis Mo.) water to 500 ml and filtering to remove particulate matter.

As used herein, the phrase "substantial sequence homology" refers to nucleotide sequences which share at least about 90% identity, and amino acid sequences which typically share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention.

The phrase "substantially the same" is used herein in reference to the nucleotide sequence of DNA, the ribonucleotide sequence of RNA, or the amino acid sequence of protein, that have slight and non-consequential sequence variations from the actual sequences disclosed herein. Species that are substantially the same are considered to be equivalent to the disclosed sequences and as such are within the scope of the appended claims. In this regard, "slight and non-consequential sequence variations" mean that sequences that are substantially the same as the DNA, RNA, or proteins disclosed and claimed herein are functionally equivalent to the human-derived sequences disclosed and claimed herein. Functionally equivalent sequences will function in substantially the same manner to produce substantially the same compositions as the human-derived nucleic acid and amino acid compositions disclosed and claimed herein. In particular, functionally equivalent DNAs encode human-derived proteins that are the same as those disclosed herein or that have conservative amino acid variations, such as substitution of a non-polar residue for another non-polar residue or a charged residue for a similarly charged residue. These changes include those recognized by those of skill in the art as those that do not substantially alter the tertiary structure of the protein.

As used herein, "$\alpha_6$ subunit DNA" refers to DNA encoding a neuronal nicotinic acetylcholine receptor subunit of the same name. Such DNA can be characterized in a number of ways, for example said DNA may encode the amino acid sequence set forth in SEQ ID NO:2, or said DNA may encode the amino acid sequence encoded by clone pcDNA3-KEalpha6.3 (as illustrated in FIG. 1).

Presently preferred $\alpha_6$-encoding DNAs can be characterized as follows said DNA may hybridize to the coding sequence set forth in SEQ ID NO:1 (preferably to substantially the entire coding sequence thereof, i.e., nucleotides 143–1624) under high stringency conditions, or said DNA may hybridize under high stringency conditions to the sequence (preferably to substantially the entire sequence) of the $\alpha_6$-encoding insert of clone pcDNA3-KEalpha6.3 (as illustrated in FIG. 1).

Especially preferred $\alpha_6$-encoding DNAs of the invention are characterized as follows DNA having substantially the same nucleotide sequence as the 6 coding region set forth in SEQ ID NO:1 (i.e., nucleotides 143–1624 thereof), or DNA having substantially the same nucleotide sequence as the $\alpha_6$-encoding insert of clone pcDNA3-KEalpha6.3 (as illustrated in FIG. 1).

Typically, unless an $\alpha_6$ subunit arises as a splice variant, $\alpha_6$-encoding DNA will share substantial sequence homology (i.e., greater than about 90%), with the $\alpha_6$ DNAs described herein. DNA or RNA encoding a splice variant may share less than 90% overall sequence homology with the DNA or RNA provided herein, but such a splice variant would include regions of nearly 100% homology to the above-described DNAs.

As used herein, a human beta subunit gene is a gene that encodes a beta subunit of a human neuronal nicotinic acetylcholine receptor. Assignment of the name "beta" to a putative neuronal nAChR subunit, according to Deneris et al. supra, is based on the lack of adjacent cysteine residues (which are characteristic of alpha subunits). The beta subunit is frequently referred to as the structural nAChR subunit (although it is possible that beta subunits also have ACh binding properties). Combination of the appropriate beta subunit(s) with appropriate alpha subunit(s) leads to the formation of a functional receptor. As used herein, a beta subunit subtype refers to a neuronal nAChR subunit that is encoded by DNA that hybridizes under high stringency conditions to at least one of the neuronal nAChR-encoding DNAs (or deposited clones) disclosed herein. A beta subunit may form a functional nAChR, as assessed by methods described herein or known to those of skill in this art, with appropriate alpha subunit subtype(s).

Also contemplated are beta subunits encoded by DNAs that encode beta subunits as defined above, but that by virtue of degeneracy of the genetic code do not necessarily hybridize to the disclosed DNA or deposited clones under the specified hybridization conditions. Such subunits may also form functional receptors, as assessed by the methods described herein or known to those of skill in the art, in combination with appropriate alpha subunit subtype(s). Typically, unless a beta subunit is encoded by RNA that arises as a splice variant, beta-encoding DNA and the beta subunit encoded thereby share substantial sequence homology with the beta-encoding DNA and beta subunit protein described herein. It is understood that DNA or RNA encoding a splice variant may share less than 90% overall homology with the DNA or RNA provided herein, but such DNA will include regions of nearly 100% homology to the DNA described herein.

As used herein, "$\beta_3$ subunit DNA" refers to DNA encoding a neuronal nicotinic acetylcholine receptor subunit of the same name. Such DNA can be characterized in a number of ways, for example, the nucleotides of said DNA may encode the amino acid sequence set forth in SEQ ID NO:4. Presently preferred $\beta_3$-encoding DNAs can be characterized as DNA which hybridizes under high stringency conditions to the coding sequence set forth in SEQ ID NO:3 (preferably to substantially the entire coding sequence thereof, i.e., nucleotides 98–1472). Especially preferred $\beta_3$-encoding DNAs of the invention are characterized as having substantially the same nucleotide sequence as set forth in SEQ ID NO:3.

Typically, unless a $\beta_3$ subunit arises as a splice variant, $\beta_3$-encoding DNA will share substantial sequence homology (greater than about 90%) with the $\beta_3$ DNAs described herein. DNA or RNA encoding a splice variant may share less than 90% overall sequence homology with the DNA or RNA provided herein, but such DNA would include regions of nearly 100% homology to the above-described DNA.

DNA encoding human neuronal nicotinic nAChR alpha and beta subunits may be isolated by screening suitable human cDNA or human genomic libraries under suitable hybridization conditions with DNA disclosed herein (including nucleotides derived from SEQ ID NOs:1 or 3). Suitable libraries can be prepared from neuronal tissue samples, basal ganglia, thalamus, hypothalamus, and the like. The library is preferably screened with a portion of DNA including the entire subunit-encoding sequence thereof, or the library may be screened with a suitable probe.

As used herein with reference to human $\alpha_6$ subunits, a probe is single-stranded DNA or RNA that has a sequence of nucleotides that includes at least 27 contiguous bases that are the same as (or the complement of) any 27 bases set forth in SEQ ID NO:1. As used herein with reference to human $\beta_3$ subunits, a probe is single-stranded DNA or RNA that has a sequence of nucleotides that includes at least 28 contiguous bases that are the same as (or the complement of) any 28 bases derived from the first 105 nucleotides of signal sequence/coding sequence set forth in SEQ ID NO:3. Preferred regions from which to construct probes include 5' and/or 3' coding sequences, sequences predicted to encode transmembrane domains, sequences predicted to encode the cytoplasmic loop, signal sequences, acetylcholine (ACh) and $\alpha$-bungarotoxin ($\alpha$-bgtx) binding sites, and the like. Amino acids that correspond to residues 190–198 of the Torpedo nAChR a subunit (see Karlin (1993) Curr. Opin. Neurobiol. 3, 299–309) are typically involved in ACh and $\alpha$-bgtx binding. The approximate amino acid residues which comprise such regions for other preferred probes are set forth in the following table:

| Subunit | Signal Sequence | TMD1* | TMD2 | TMD3 | TMD4 | Cytoplasmic Loop |
|---|---|---|---|---|---|---|
| $\alpha_6$ | 1–30 | 240–265 | 272–294 | 301–326 | 458–483 | 327–457 |
| $\beta_3$ | 1–20 | 231–258 | 265–287 | 293–318 | 421–446 | 319–420 |

*TMD = transmembrane domain

Alternatively, portions of the DNA can be used as primers to amplify selected fragments in a particular library.

After screening the library, positive clones are identified by detecting a hybridization signal; the identified clones are characterized by restriction enzyme mapping and/or DNA sequence analysis, and then examined, by comparison with the sequences set forth herein or with the deposited clones described herein, to ascertain whether they include DNA encoding a complete alpha or beta subunit. If the selected clones are incomplete, they may be used to rescreen the same or a different library to obtain overlapping clones. If desired, the library can be rescreened with positive clones. until overlapping clones that encode an entire alpha or beta subunit are obtained. If the library is a cDNA library, then the overlapping clones will include an open reading frame. If the library is genomic, then the overlapping clones may include exons and introns. In both instances, complete clones may be identified by comparison with the DNA and encoded proteins provided herein.

Complementary DNA clones encoding various subtypes of human neuronal nAChR alpha and beta subunits have been isolated. Each subtype of the subunit appears to be encoded by a different gene. The DNA clones provided herein may be used to isolate genomic clones encoding each subtype and to isolate any splice variants by screening libraries prepared from different neural tissues. Nucleic acid amplification techniques, which are well known in the art, can be used to locate splice variants of human neuronal nAChR subunits. This is accomplished by employing oligonucleotides based on DNA sequences surrounding divergent sequence(s) as primers for amplifying human RNA or genomic DNA. Size and sequence determinations of the amplification products can reveal the existence of splice variants. Furthermore, isolation of human genomic DNA sequences by hybridization can yield DNA containing multiple exons, separated by introns, that correspond to different splice variants of transcripts encoding human neuronal nAChR subunits.

It has been found that not all subunit subtypes are expressed in all neural tissues or in all portions of the brain. Thus, in order to isolate cDNA encoding particular subunit subtypes or splice variants of such subtypes, it is preferable to screen libraries prepared from different neuronal or neural tissues. Preferred libraries for obtaining DNA encoding each subunit include: substantia nigra, thalamus or hypothalamus to isolate human $\alpha_6$-encoding DNA and substantia nigra or thalamus to isolate human $\beta_3$-encoding DNA.

The above-described nucleotide sequences can be incorporated into vectors for further manipulation. As used herein, vector (or plasmid) refers to discrete elements that are used to introduce heterologous DNA into cells for either expression or replication thereof. Selection and use of such vehicles are well within the level of skill of the art.

An expression vector includes vectors capable of expressing DNAs that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, allows expression of DNA cloned into the appropriate site on the vector. Appropriate expression vectors are well known to those of skill in the art and include those that are replicable in eukaryotic cells and/or prokaryotic cells and those that remain episomal or those which integrate into the host cell genome. Presently preferred plasmids for expression of invention nAChR subunits in eukaryotic host cells, particularly mammalian cells, include cytomegalovirus (CMV), Simian virus 40 (SV40) and mouse mammary tumor virus (MMTV) promoter-containing vectors such as pCMV, pcDNA1, pcDNA3, pZeoSV, pCEP4, pMAMneo, pMAMhyg, and the like.

As used herein, a promoter region refers to a segment of DNA that controls transcription of DNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove or alter 5' untranslated portions of the clones to remove extra, potential alternative translation initiation (i.e., start) codons or other sequences that interfere with or reduce expression, either at the level of transcription or translation. Alternatively, consensus ribosome binding sites (see, for example, Kozak (1991) J. Biol. Chem. 266:19867–19870) can be inserted immediately 5' of the start codon to enhance expression. The desirability of (or need for) such modification may be empirically determined.

As used herein, expression refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

Particularly preferred vectors for transfection of mammalian cells are the SV40 promoter-based expression vectors, such as pZeoSV (Invitrogen, San Diego, Calif.) CMV promoter-based vectors such as pcDNA1, pcDNA3, pCEP4 (Invitrogen, San Diego, Calif.), and MMTV promoter-based vectors such as pMAMneo (Clontech, Inc.).

Full-length DNAs encoding human neuronal nAChR subunits have been inserted into vector pcDNA3, a pUC19-based mammalian cell expression vector containing the CMV promoter/enhancer, a polylinker downstream of the CMV promoter/enhancer, followed by a bovine growth hormone (BGH) polyadenylation signal. Placement of nAChR subunit DNA between the CMV promoter and BGH polyadenylation signal provides for constitutive expression of the foreign DNA in a mammalian host cell transfected with the construct. For inducible expression of human nAChR subunit-encoding DNA in a mammalian cell, the DNA can be inserted into a plasmid such as pMAMneo. This plasmid contains the mouse mammary tumor virus (MMTV) promoter for steroid-inducible expression of operatively associated foreign DNA. If the host cell does, not express endogenous glucocorticoid receptors required for uptake of glucorcorticoids (i.e., inducers of the MMTV promoter) into the cell, it is necessary to additionally transfect the cell with DNA encoding the glucocorticoid receptor (ATCC accession no. 67200).

In accordance with another embodiment of the present invention, there are provided cells containing the above-described polynucleic acids (i.e., DNA or mRNA). Such host cells as bacterial, yeast and mammalian cells can be used for replicating DNA and producing nAChR subunit(s). Methods for constructing expression vectors, preparing in vitro transcripts, transfecting DNA into mammalian cells, injecting oocytes, and performing electrophysiological and other analyses for assessing receptor expression and function as described herein are also described in PCT Application Nos. PCT/US91/02311, PCT/US91/05625 and PCT/US92/11090, and in co-pending U.S. application Ser. Nos.

07/504,455, 07/563,751 and 07/812,254. The subject matter of these applications are hereby incorporated by reference herein in their entirety.

Incorporation of cloned DNA into a suitable expression vector, transfection of eukaryotic cells with one or a combination of expression constructs encoding one or more distinct genes or with linear DNA, and selection of transfected cells are well known in the art (see, e.g., Sambrook et al. (1989) supra). Heterologous DNA may be introduced into host cells by any method known to those of skill in the art, such as transfection with an expression construct encoding the heterologous DNA by $CaPO_4$ precipitation (see, e.g., Wigler et al. (1979) Proc. Natl. Acad. Sci. 76:1373–1376). Recombinant cells can then be cultured under conditions whereby the subunit(s) encoded by the DNA is (are) expressed. Preferred cells include mammalian cells (e.g., HEK 293, CHO and Ltk⁻ cells), yeast cells (e.g., methylotrophic yeast cells, such as *Pichia pastoris*), bacterial cells (e.g., *Escherichia coli*), and the like.

While the DNA provided herein may be expressed in any eukaryotic cell, including yeast cells (such as, for example, *P. pastoris* (see U.S. Pat. Nos. 4,882,279, 4,837,148, 4,929, 555 and 4,855,231), *Saccharomyces cerevisiae, Candida tropicalis, Hansenula polymorpha,* and the like), mammalian expression systems, including commercially available systems and other such systems known to those of skill in the art, for expression of DNA encoding the human neuronal nicotinic nAChR subunits provided herein are presently preferred. Xenopus oocytes are preferred for expression of RNA transcripts of the DNA.

In preferred embodiments, DNA is ligated into a vector, and the resulting construct is introduced into suitable host cells to produce transformed cell lines that express a specific human neuronal nAChR receptor subtype, or specific combinations of subtypes. The resulting cell lines can then be produced in quantity for reproducible quantitative analysis of the effects of drugs on receptor function. In other embodiments, mRNA may be produced by in vitro transcription of DNA encoding each subunit. This mRNA, either from a single subunit clone or from a combination of clones, can then be injected into Xenopus oocytes where the mRNA directs the synthesis of the human receptor subunits, which then form functional receptors. Alternatively, the subunit-encoding DNA can be directly injected into oocytes for expression of functional receptors. The transfected mammalian cells or injected oocytes may then be used in the methods of drug screening provided herein.

Cloned full-length DNA encoding any of the subunits of human neuronal nicotinic nAChR may be introduced into a plasmid vector for expression in a eukaryotic cell. Such DNA may be genomic DNA or cDNA. Host cells may be transfected with one or a combination of plasmids, each of which encodes at least one human neuronal nAChR subunit.

Eukaryotic cells in which DNA or RNA may be introduced include any cells that are transfectable by such DNA or RNA or into which such DNA or RNA may be injected. Preferred cells are those that can be transiently or stably transfected and also express the DNA and RNA. Presently most preferred cells are those that can form recombinant or heterologous human neuronal nicotinic nAChRs comprising one or more subunits encoded by the heterologous DNA. Such cells may be identified empirically or selected from among those known to be readily transfected or injected.

Exemplary cells for introducing DNA include cells of mammalian origin (e.g., COS cells, mouse L cells, Chinese hamster ovary (CHO) cells, human embryonic kidney (HEK) cells, GH3 cells and other such cells known to those of skill in the art), amphibian cells (e.g., *Xenopus laevis* oöcytes), yeast cells (e.g., *Saccharomyces cerevisiae, Pichia pastoris*), and the like. Exemplary cells for expressing injected RNA transcripts include *Xenopus laevis* oöcytes. Cells that are preferred for transfection of DNA are known to those of skill in the art or may be empirically identified, and include HEK 293 (which are available from ATCC under accession #CRL 1573); Ltk⁻ cells (which are available from ATCC under accession #CCL1.3);

COS-7 cells (which are available from ATCC under accession #CRL 1651); and GH3 cells (which are available from ATCC under accession #CCL82.1). Presently preferred cells include GH3 cells and HEK 293 cells, particularly HEK 293 cells that have been adapted for growth in suspension and that can be frozen in liquid nitrogen and then thawed and regrown. HEK 293 cells are described, for example, in U.S. Pat. No. 5,024,939 to Gorman (see, also, Stillman et al. (1985) Mol. Cell. Biol. 5:2051–2060).

DNA may be stably incorporated into cells or may be transiently introduced using methods known in the art. Stably transfected mammalian cells may be prepared by transfecting cells either with one or more expression constructs carrying DNA encoding nAChR subunits and a separate expression vector carrying a selectable marker gene (e.g., the gene for neomycin resistance, zeocin resistance, hygromycin resistance and the like) or with one or more expression constructs which carry both the DNA encoding nAChR subunit and the selectable marker, and growing the transfected cells under conditions selective for cells expressing the marker gene(s). To produce such cells, the cells should be transfected with a sufficient concentration of subunit-encoding nucleic acids to form human neuronal nAChRs that contain the human subunits encoded by heterologous DNA. The precise amounts and ratios of DNA encoding the subunits may be empirically determined and optimized for a particular combination of subunits, cells and assay conditions. Recombinant cells that express neuronal nAChR containing subunits encoded only by the heterologous DNA or RNA are especially preferred.

Heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan. Similarly, the human neuronal nicotinic nAChR subunits may be purified using protein purification methods known to those of skill in the art. For example, antibodies or other ligands that specifically bind to one or more of the subunits may be used for affinity purification of the subunit or human neuronal nAChRs containing the subunits.

In accordance with one embodiment of the present invention, methods for producing cells that express human neuronal nAChR subunits and functional receptors are also provided. In one such method, host cells are transfected with DNA encoding at least one alpha subunit of a neuronal nAChR and at least one beta subunit of a neuronal nAChR. Using methods such as northern blot or slot blot analysis, transfected cells that contain alpha and/or beta subunit encoding DNA or RNA can be selected. Transfected cells are also analyzed to identify those that express nAChR protein. Analysis can be carried out, for example, by measuring the ability of cells to bind acetylcholine, nicotine, or a nAChR agonist, compared to the nicotine binding ability of untransfected host cells or other suitable control cells, by electrophysiologically monitoring the currents through the cell membrane in response to a nAChR agonist, and the like.

In particularly preferred aspects, eukaryotic cells which contain heterologous DNAs express such DNA and form recombinant functional neuronal nAChR(s). In more preferred aspects, recombinant neuronal nAChR activity is readily detectable because it is a type that is absent from the untransfected host cell or is of a magnitude not exhibited in the untransfected cell. Such cells that contain recombinant receptors could be prepared, for example, by causing cells transformed with DNA encoding the human neuronal nicotinic nAChR $\alpha_6$ and $\beta_3$ subunits to express the corresponding proteins in the presence or absence of one or more alpha and/or beta nAChR subunits. The resulting synthetic or recombinant receptor would contain the $\alpha_6$ and $\beta_3$ nAChR subunits. Such a receptor would be useful for a variety of applications, e.g., as part of an assay system free of the interferences frequently present in prior art assay systems employing non-human receptors or human tissue preparations. Furthermore, testing of single receptor subunits with a variety of potential agonists or antagonists would provide additional information with respect to the function and activity of the individual subunits. Such information may lead to the identification of compounds which are capable of very specific interaction with one or more of the receptor subunits. Such specificity may prove of great value in medical application.

Thus, DNA encoding one or more human neuronal nAChR subunits may be introduced into suitable host cells (e.g., eukaryotic or prokaryotic cells) for expression of individual subunits and functional nAChRs. Preferably combinations of alpha and beta subunits may be introduced into cells: such combinations include combinations of any one or more of $\alpha_2$, $\alpha_3$, $\alpha_4$, $\alpha_5$, $\alpha_6$ and $\alpha_7$ with $\beta_2$, $\beta_3$ and/or $\beta_4$. Sequence information for a is presented in Proc. Natl. Acad. Sci.USA (1992) 89:1572–1576; sequence information for $\alpha_2$, $\alpha_3$, $\alpha_4$, $\alpha_7$, $\beta_2$ and $\beta_4$ is presented in PCT publication WO 94/20617, incorporated by reference herein; and sequence information for $\alpha_6$ and $\beta_3$ is presented in the Sequence Listing provided herewith. Presently preferred combinations of subunits include $\alpha_6$ and/or $\beta_3$ with any one or more of $\alpha_2$, $\alpha_3$, $\alpha_4$, $\alpha_5$, $\alpha_7$, $\beta_2$ or $\beta_4$. It is recognized that some of the subunits may have ion transport function in the absence of additional subunits, while others require a combination of two or more subunits in order to display ion transport function. For example, the $\alpha_7$ subunit is functional in the absence of any added beta subunit. Furthermore, some of the subunits may not form functional nAChRs alone or in combination, but instead may modulate the properties of other nAChR subunit combinations.

In certain embodiments, eukaryotic cells with heterologous human neuronal nAChRs are produced by introducing into the cell a first composition, which contains at least one RNA transcript that is translated in the cell into a subunit of a human neuronal nAChR. In preferred embodiments, the subunits that are translated include an alpha subunit of a human neuronal nAChR. More preferably, the composition that is introduced contains an RNA transcript which encodes an alpha subunit and also contains an RNA transcript which encodes a beta subunit of a human neuronal nAChR. RNA transcripts can be obtained from cells transfected with DNAs encoding human neuronal nAChR subunits or by in vitro transcription of subunit-encoding DNAs. Methods for in vitro transcription of cloned DNA and injection of the resulting mRNA into eukaryotic cells are well known in the art. Amphibian oocytes are particularly preferred for expression of in vitro transcripts of the human neuronal nAChR DNA clones provided herein. See, for example, Dascal (1989) CRC Crit. Rev. Biochem. 22:317–387, for a review of the use of Xenopus oocytes to study ion channels.

Thus, stepwise introduction into cells of DNA or RNA encoding one or more alpha subtypes, and one or more beta subtypes is possible. The resulting cells may be tested by the methods provided herein or known to those of skill in the art to detect functional nAChR activity. Such testing will allow the identification of combinations of alpha and beta subunit subtypes that produce functional nAChRs, as well as individual subunits that produce functional nAChRs.

As used herein, activity of a human neuronal nAChR refers to any activity characteristic of an nAChR. Such activity can typically be measured by one or more in vitro methods, and frequently corresponds to an in vivo activity of a human neuronal nAChR. Such activity may be measured by any method known to those of skill in the art, such as, for example, measuring the amount of current which flows through the recombinant channel in response to a stimulus.

Methods to determine the presence and/or activity of human neuronal nAChRs include assays that measure nicotine binding, $^{86}$Rb ion-flux, $Ca^{2+}$ influx, the electrophysiological response of cells, the electrophysiological response of oocytes injected with RNA, and the like. In particular, methods are provided herein for the measurement or detection of an nAChR-mediated response upon contact of cells containing the DNA or mRNA with a test compound.

As used herein, a recombinant or heterologous human neuronal nAChR refers to a receptor that contains one or more subunits encoded by heterologous DNA that has been introduced into and expressed in cells capable of expressing receptor protein. A recombinant human neuronal nAChR may also include subunits that are produced by DNA endogenous to the host cell. In certain embodiments, recombinant or heterologous human neuronal nAChR may contain only subunits that are encoded by heterologous DNA.

As used herein, heterologous or foreign DNA and RNA are used interchangeably and refer to DNA or RNA that does not occur naturally as part of the genome of the cell in which it is present or to DNA or RNA which is found in a location or locations in the genome that differ from that in which it occurs in nature. Typically, heterologous or foreign DNA and RNA refers to DNA or RNA that is not endogenous to the host cell and has been artificially introduced into the cell. Examples of heterologous DNA include DNA that encodes a human neuronal nAChR subunit, DNA that encodes RNA or proteins that mediate or alter expression of endogenous DNA by affecting transcription, translation, or other regulatable biochemical processes, and the like. The cell that expresses heterologous DNA may contain DNA encoding the same or different expression products. Heterologous DNA need not be expressed and may be integrated into the host cell genome or maintained episomally.

Recombinant receptors on recombinant eukaryotic cell surfaces may contain one or more subunits encoded by the DNA or mRNA encoding human neuronal nAChR subunits, or may contain a mixture of subunits encoded by the host cell and subunits encoded by heterologous DNA or mRNA. Recombinant receptors may be homogeneous or may be a mixture of subtypes. Mixtures of DNA or mRNA encoding receptors from various species, such as rats and humans, may also be introduced into the cells. Thus, a cell may be prepared that expresses recombinant receptors containing only $\alpha_6$ and $\beta_3$ subunits, or in combination with any other alpha and beta subunits provided herein. For example, either or both of the $\alpha_6$ and $\beta_3$ subunits of the present invention can be co-expressed with $\alpha_2$, $\alpha_3$, $\alpha_4$, $\alpha_5$, $\alpha_7$, $\beta_2$ and/or $\beta_4$ receptor subunits. As noted previously, some of the neuronal nAChR subunits may be capable of forming functional receptors in the absence of other subunits, thus co-expression is not always required to produce functional receptors. Moreover, some nAChR subunits may require co-expression with two or more nAChR subunits to participate in functional receptors.

As used herein, a functional neuronal nAChR is a receptor that exhibits an activity of neuronal nicotinic nAChRs as assessed by any in vitro or in vivo assay disclosed herein or known to those of skill in the art. Possession of any such activity that may be assessed by any method known to those of skill in the art and provided herein is sufficient to designate a receptor as functional. Methods for detecting nAChR protein and/or activity include, for example, assays that measure nicotine binding, $^{86}$Rb ion-flux, $Ca^{2+}$ influx, the electrophysiological response of cells containing heterologous DNA or mRNA encoding one or more receptor subunit subtypes, and the like. Since all combinations of alpha and beta subunits may not form functional receptors, numerous combinations of alpha and beta subunits should be tested in order to fully characterize a particular subunit and cells which produce same. Thus, as used herein, "functional" with respect to a recombinant or heterologous human neuronal nAChR means that the receptor channel is able to provide for and regulate entry of human neuronal nAChR-permeable ions, such as, for example, $Na^+$, $K^+$, $Ca^{2+}$ or $Ba^{2+}$, in response to a stimulus and/or bind ligands with affinity for the receptor. Preferably such human neuronal nAChR activity is distinguishable, such as by electrophysiological, pharmacological and other means known to those of skill in the art, from any endogenous nAChR activity that may be produced by the host cell.

In accordance with a particular embodiment of the present invention, recombinant human neuronal nAChR-expressing mammalian cells or oocytes can be contacted with a test compound, and the modulating effect(s) thereof can then be evaluated by comparing the nAChR-mediated response in the presence and absence of test compound, or by comparing the nAChR-mediated response of test cells, or control cells (i.e., cells that do not express neuronal nAChRs), to the presence of the compound.

As used herein, a compound or signal that "modulates the activity of a neuronal nAChR" refers to a compound or signal that alters the activity of nAChR so that activity of the nAChR is different in the presence of the compound or signal than in the absence of the compound or signal. In particular, such compounds or signals include agonists and antagonists. The term agonist refers to a substance or signal, such as ACh, that activates receptor function; and the term antagonist refers to a substance that interferes with receptor function. Typically, the effect of an antagonist is observed as a blocking of activation by an agonist. Antagonists include competitive and non-competitive antagonists. A competitive antagonist (or competitive blocker) interacts with or near the site specific for the agonist (e.g., ligand or neurotransmitter) for the same or closely situated site. A non-competitive antagonist or blocker inactivates the functioning of the receptor by interacting with a site other than the site that interacts with the agonist.

As understood by those of skill in the art, assay methods for identifying compounds that modulate human neuronal nAChR activity (e.g., agonists and antagonists) generally require comparison to a control. One type of a "control" cell or "control" culture is a cell or culture that is treated substantially the same as the cell or culture exposed to the test compound, except the control culture is not exposed to test compound. For example, in methods that use voltage clamp electrophysiological procedures, the same cell can be tested in the presence and absence of test compound, by merely changing the external solution bathing the cell. Another type of "control" cell or "control" culture may be a cell or a culture of cells which are identical to the transfected cells, except the cells employed for the control culture do not express functional human neuronal nAChRs. In this situation, the response of test cell to test compound is compared to the response (or lack of response) of receptor-negative (control) cell to test compound, when cells or cultures of each type of cell are exposed to substantially the same reaction conditions in the presence of compound being assayed.

Functional recombinant human neuronal nAChRs include at least an alpha subunit, or at least an alpha subunit and a beta subunit of a human neuronal nAChR. Eukaryotic cells expressing these subunits have been prepared by injection of RNA transcripts and by transfection of DNA. Such cells have exhibited nAChR activity attributable to human neuronal nAChRs that contain one or more of the heterologous human neuronal nAChR subunits.

With respect to measurement of the activity of functional heterologous human neuronal nAChRs, endogenous nAChR activity and, if desired, activity of nAChRs that contain a mixture of endogenous host cell subunits and heterologous subunits, should, if possible, be inhibited to a significant extent by chemical, pharmacological and electrophysiological means.

The invention will now be described in greater detail with reference to the following non-limiting examples.

EXAMPLE 1

Isolation of DNA Encoding Human nAChR $\alpha_6$ Subunits

A human substantia nigra cDNA library (Clontech Laboratories, Inc.) was screened for hybridization to a fragment of the rat nAChR $\alpha_6$ subunit cDNA. Isolated plaques were transferred to nitrocellulose filters and hybridization was performed in 5×Denhardt's, 5×SSPE, 50% formamide, 200 µg/ml denatured salmon sperm DNA and 0.2% SDS, at 42° C. Washes were performed in 0.2×SSPE, 0.2% SDS, at 60° C.

Five hybridizing clones were plaque-purified and characterized by restriction endonuclease mapping and DNA sequence analysis. The DNA sequence of the 5'- and 3'-ends of the cDNA inserts was determined using commercially available λgt10 forward and reverse oligonucleotide primers. Analysis of the DNA sequence of the five cDNA inserts revealed that three clones contained the translational initiation codon, a full-length $\alpha_6$ open reading frame (nucleotides 143–1624 of SEQ ID NO:1), the translational stop codon and 142 additional nucleotides of 5'- and 116 nucleotides of 3'-flanking sequences. The amino acid sequence deduced from the nucleotide sequence of the full-length clone has 82% identity with the amino acid sequence deduced from the rat nAChR $\alpha_6$ subunit DNA. Several regions of the deduced rat and human $\alpha_6$ amino acid sequences are notably dissimilar:

amino acids 1–30 (the human signal sequence has only ~56% identity with respect to the rat sequence),
amino acids 31–50 (the human sequence has only ~70% identity with respect to the rat sequence),
amino acids 344–391 (the human sequence has only ~40% identity with respect to the rat sequence),
amino acids 401–428 (the human sequence has only ~64% identity with respect to the rat sequence).

Furthermore, the insert DNA of a single clone, KEα6.5, was determined to be missing 45 nucleotides of $\alpha_6$ coding sequence, resulting in an in-frame deletion of 15 amino acid residues of the deduced amino acid sequence (residues 74 to 88 of SEQ ID NO:2). Interestingly, the deduced amino acid sequence immediately downstream of the site of the deletion shares only ~58% amino acid identity with the deduced rat $\alpha_6$ amino acid sequence (amino acids 89–100 of SEQ ID NO:2).

EXAMPLE 2

Isolation of DNA Encoding Human Neuronal nAChR $\beta_3$ Subunit

A human substantia nigra CDNA library (Clontech Laboratories, Inc.) was screened for hybridization to synthetic oligonucleotide primers complementary to the C-terminus of human nicotinic nAChR $\beta_3$ subunit cDNA. Isolated plaques were transferred to nitrocellulose filters and hybridized under high stringency conditions with respect to oligonucleotides (washing conditions 1×SSPE, 0.2% SDS at 50° C.) with synthetic oligonucleotide primers complementary to the partial human $\beta_3$ nAChR subunit described by Willoughby et al., (1993) Neurosci. Lett. 155, 136–139.

Two hybridizing clones were plaque-purified and characterized by restriction endonuclease mapping. The DNA sequence of the 5'- and 3'-ends of the cDNA insert was determined using commercially available T7 and SP6 oligonucleotide primers. The complete sequence of clone KBβ3.2 was determined. Clone KBβ3.2 contains a 1927 bp cDNA insert that contains a 1,377 nucleotide open reading frame encoding a full-length $\beta_3$ nAChR subunit (nucleotides 98–1472 SEQ ID NO:3) as well as 97 nucleotides of 5'- and 453 nucleotides of 3'-untranslated sequences. The amino acid sequence deduced from the nucleotide sequence of the full-length clone has ~81% identity with the amino acid sequence deduced from the rat nicotinic nAChR $\beta_3$ subunit DNA. Several regions of the deduced rat and human $\beta_3$ amino acid sequences are notably dissimilar:

amino acids 1–28 (the human signal sequence has only ~25% identity with respect to the rat sequence), amino acids 347–393 (the human sequence has only ~55% identity with respect to the rat sequence), amino acids 440–464 (the human sequence has only ~68% identity with respect to the rat sequence).

EXAMPLE 3

Preparation of Constructs for the Expression of Recombinant Human Neuronal nAChR Subunits Isolated cDNAs encoding human neuronal nAChR subunits were incorporated into vectors for use in expressing the subunits in mammalian host cells and for use in generating in vitro transcripts from the DNAs to be expressed in Xenopus oocytes. The following vectors were utilized in preparing the constructs.

A. Constructs for Expressing Human nAChR $\alpha_6$ Subunits

A 1,743 bp EcoRI fragment, encoding a full-length ACh $\alpha_6$ subunit, was isolated from KEα6.3 by standard methods and ligated into the EcoRI polylinker site of the vector pcDNA3 to generate pcDNA3-KEα6.3 (see FIG. 1). Plasmid pcDNA3 (see FIG. 1) is a pUC19-based vector that contains a CMV promoter/enhancer, a T7 bacteriophage RNA polymerase promoter positioned downstream of the CMV promoter/enhancer, a bovine growth hormone (BGH) polyadenylation signal downstream of the T7 promoter, and a polylinker between the T7 promoter and the BGH polyadenylation signal. This vector thus contains all of the regulatory elements required for expression in a mammalian host cell of heterologous DNA which has been incorporated into the vector at the polylinker. In addition, because the T7 promoter is located just upstream of the polylinker, this plasmid can be used for the synthesis of in vitro transcripts of heterologous DNA that has been subcloned into the vector at the polylinker. Furthermore, this plasmid contains a gene encoding neomycin resistance used as a selectable marker during transfection. FIG. 1 also shows a partial restriction map of pcDNA3-KEα6.3.

The expression of the full-length human nAChR $\alpha_6$ subunit was optimized by the introduction of a consensus ribosome binding site (RBS; Kozak, 1991) prior to the translational start codon. The existing 5'-untranslated region was modified by PCR mutagenesis using the plasmid pcDNA3-KEα6.3 as a DNA template and a complementary upstream oligonucleotide containing the appropriate nucleotide RBS substitutions as well as flanking 5' HindIII and EcoRI sites, and an oligonucleotide complementary to a $\alpha_6$ coding sequences ~450 nucleotides downstream of the translational start codon. The resulting PCR fragment contained HindIII and EcoRI sites followed by the consensus RBS and nucleotides 1–459 of the human ACh $\alpha_6$ coding sequence (nucleotides 143–602 of SEQ ID NO:1). The amplified DNA was digested with HindIII and BamHI; the 308 bp HindIII-BamHI fragment was isolated and ligated with the 5.3 kb BamHI-PvuI fragment of pcDNA3-KE6.3 and the 1.4 kb PvuI to HindIII fragment from pcDNA3 to generate the ~7.0 kb plasmid pcDNA3-KEα6RBS.

B. Constructs for Expressing Human Neuronal nAChR $\beta_3$ Subunits

Figure 2:
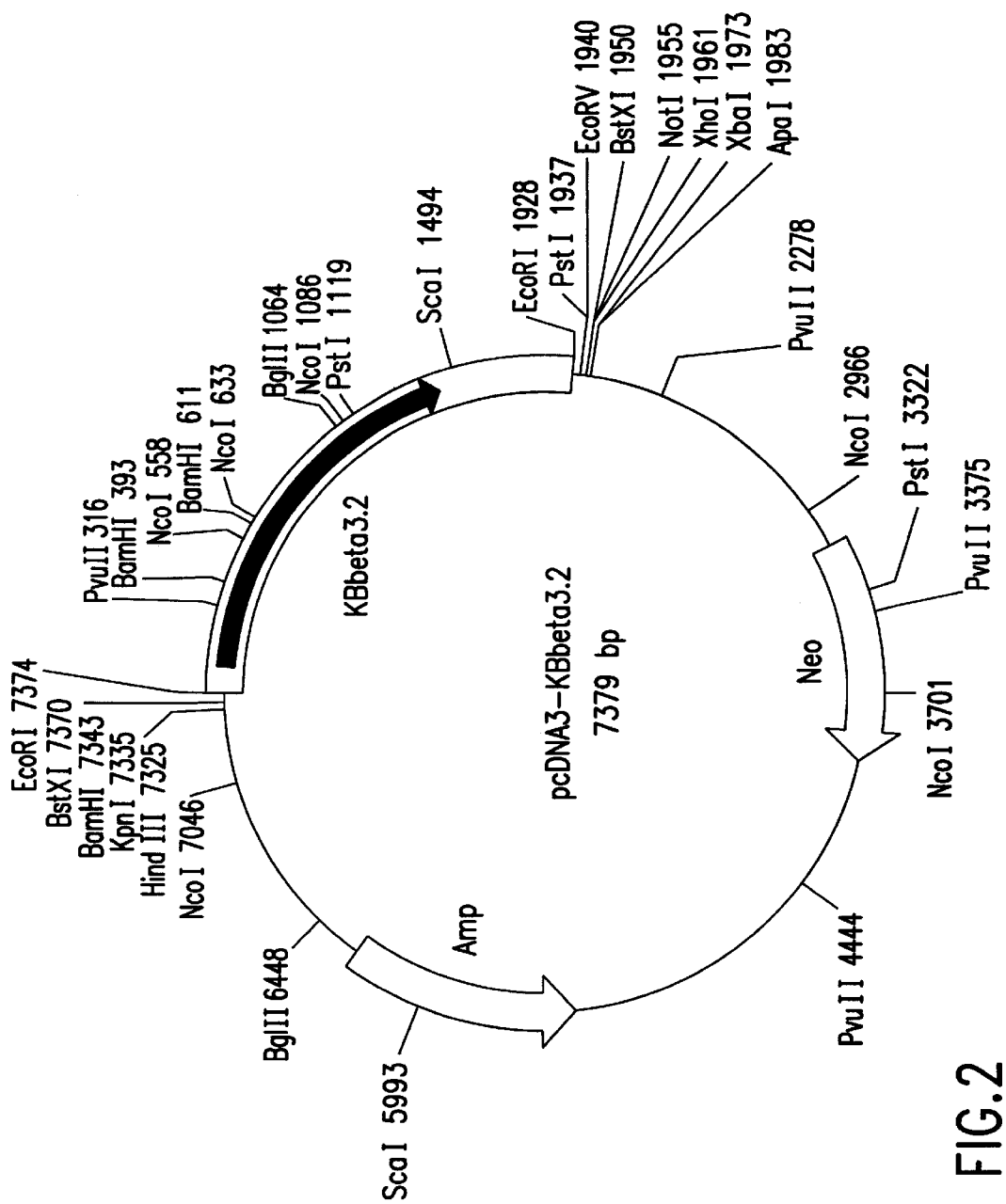
FIG. 2 presents a restriction map of a CMV promoter-based vector, pcDNA3-KEbeta3.2, which contains a $\beta_3$-encoding sequence as an EcoRI insert.

An ~2.0 kb EcoRI fragment, encoding a full-length nicotinic ACh $\beta_3$ subunit, was isolated from KEβ3.2 by standard methods and ligated into the EcoRI polylinker site of the vector pcDNA3 to generate pcDNA3-KEβ3.2 (see FIG. 2). FIG. 2 also shows a partial restriction map of PcDNA3-KEβ3.2.

The expression of the full-length human nicotinic nAChR 3 subunit is optimized by the introduction of a consensus ribosome binding site (RBS) prior to the translational start codon. The existing 5'-untranslated region is modified by PCR mutagenesis using a method similar to that described above for the $\alpha_6$ nAChR subunit.

EXAMPLE 4

Expression of Recombinant Human Neuronal nAChR in Oocytes

Xenopus oocytes are injected with in vitro transcripts prepared from constructs containing DNA encoding $\alpha_6$ and $\beta_3$ subunits. Electrophysiological measurements of the oocyte transmembrane currents are made using the two-electrode voltage clamp technique (see, e.g., Stuhmer (1992) Meth. Enzymol. 207:319–339).

1. Preparation of in vitro transcripts

Recombinant capped transcripts of pcDNA3-KEα6RBS and pcDNA3-KBβ3RBS are synthesized from linearized plasmids using the mMessage and mMachine in vitro transcription kit according to the capped transcript protocol provided by the manufacturer (Catalog 1344 from AMBION, Inc., Austin, Tex.). The mass of each synthesized transcript is determined by UV absorbance and the integrity of each transcript is determined by electrophoresis through an agarose gel.

2. Electrophysiology

Xenopus oocytes are injected with either 12.5, 50 or 125 ng of one or more human nicotinic nAChR $\alpha$ and $\beta$ subunit transcript per oocyte. The preparation and injection of oocytes is carried out as described by Dascal (1987) in *Crit. Rev. Biochem.* 22:317–387. Two-to-six days following mRNA injection, the oocytes are examined using the two-electrode voltage clamp technique. The cells are bathed in Ringer's solution (115 mM NaCl, 2.5 mM KCl, 1.8 mM $CaCl_2$, 10 mM HEPES, pH 7.3) containing 1 µM atropine with or without 100 µM d-tubocurarine. Cells are seen to be voltage-clamped at −60 to −80 mV. Data are acquired with Axotape software at 2–5 Hz. The agonists acetylcholine (ACh), nicotine, and cytisine are added at concentrations ranging from 0.1 µM to 100 µM.

EXAMPLE 5

Recombinant Expression of Human nAChR Subunits in Mammalian Cells

Human embryonic kidney (HEK) 293 cells are transiently and stably transfected with DNA encoding human neuronal nicotinic nAChR $\alpha_6$ and $\beta_3$ subunits. Transient transfectants are analyzed for expression of nicotinic nAChR using various assays, e.g., electrophysiological methods, $Ca^{2+}$-sensitive fluorescent indicator-based assays.

1. Transient Transfection of HEK Cells

HEK cells are transiently co-transfected with DNA encoding one or more α subunit and/or one or more β subunits. Approximately $2 \times 10^6$ HEK cells are transiently transfected with 18 µg of the indicated plasmid(s) according to standard $CaPO_4$ transfection procedures [Wigler et al. (1979) *Proc. Natl. Acad. Sci. USA* 76:1373–1376] or using lipofectamine according to the manufacturer's instructions (Bethesda Research Laboratory (BRL), Gaithersburg, Md.). In addition, 2 4 µg of plasmid pCMVβgal (Clontech Laboratories, Palo Alto, Calif.), which contains the *Escherichia coli* β-galactosidase gene fused to the CMV promoter, are co-transfected as a reporter gene for monitoring the efficiency of transfection. The transfectants are analyzed for β-galactosidase expression by measurement of β-galactosidase activity [Miller (1972) *Experiments in Molecular Genetics*, pp.352–355, Cold Spring Harbor Press]. Transfectants can also be analyzed for β-galactosidase expression by direct staining of the product of a reaction involving β-galactosidase and the X-gal substrate [Jones (1986) *EMBO* 5:3133–3142].

2. Stable Transfection of HEK Cells

HEK cells are transfected using the calcium phosphate transfection procedure [*Current Protocols in Molecular Biology*, Vol. 1, Wiley Inter-Science, Supplement 14, Unit 9.1.1–9.1.9 (1990)]. HEK cells are transfected with 1 ml of DNA/calcium phosphate precipitate containing the DNA encoding the desired alpha and beta subunits and pSV2neo (as a selectable marker). After 14 days of growth in medium containing 1 µg/ml G418, colonies form and are individually isolated by using cloning cylinders. The isolates are subjected to limiting dilution and screened to identify those that expressed the highest level of nAChR, as described below.

3. Analysis of Transfectants a. Fluorescent indicator-based assays

Activation of the ligand-gated nAChR by agonists leads to an influx of cations, including $Ca^{++}$, through the receptor channel. $Ca^{++}$ entry into the cell through the channel can induce release of calcium contained in intracellular stores. Monovalent cation entry into the cell through the channel can also result in an increase in cytoplasmic $Ca^{++}$ levels through depolarization of the membrane and subsequent activation of voltage-dependent calcium channels. Therefore, methods of detecting transient increases in intracellular calcium concentration can be applied to the analysis of functional nicotinic nAChR expression. One method for measuring intracellular calcium levels relies on calcium-sensitive fluorescent indicators.

Calcium-sensitive indicators, such as fluo-3 (Catalog No. F-1241, Molecular Probes, Inc., Eugene, Oreg.), are available as acetoxymethyl esters which are membrane permeable. When the acetoxymethyl ester form of the indicator enters a cell, the ester group is removed by cytosolic esterases, thereby trapping the free indicator in the cytosol. Interaction of the free indicator with calcium results in increased fluorescence of the indicator; therefore, an increase in the intracellular $Ca^{2+}$ concentration of cells containing the indicator can be expressed directly as an increase in fluorescence. An automated fluorescence detection system for assaying nicotinic nAChR has been described in commonly assigned pending U.S. patent application Ser. No. 07/812,254 and corresponding PCT Patent Application No. US92/11090.

HEK cells that are transiently or stably co-transfected with DNA encoding appropriate α and/or β subunits and $\alpha_6$ and $\beta_3$ subunits are analyzed for expression of functional recombinant nAChR using the automated fluorescent indicator-based assay. The assay procedure is as follows.

Untransfected HEK cells and HEK cells co-transfected with the appropriate α and β subunits are plated in the wells of a 96-well microtiter dish and loaded with fluo-3 by incubation for 2 hours at 20° C. in a medium containing 20 µM fluo-3, 0.2% Pluronic F-127 in HBS (125 mM NaCl, 5 mM KCl, 1.8 mM $CaCl_2$, 0.62 mM $MgSO_4$, 6 mM glucose, 20 mM HEPES, pH 7.4). The cells are then washed with assay buffer (i.e., HBS). The antagonist d-tubocurarine is added to some of the wells at a final concentration of 10 µM. The microtiter dish is then placed into a fluorescence plate reader and the basal fluorescence of each well is measured and recorded before addition of agonist, e.g., 200 µM nicotine, to the wells. The fluorescence of the wells is monitored repeatedly during a period of approximately 60 seconds following addition of nicotine.

The fluorescence of the untransfected HEK cells does not change after addition of nicotine. In contrast, the fluorescence of the co-transfected cells, in the absence of d-tubocurarine, increases dramatically after addition of nicotine to the wells. This nicotine-stimulated increase in fluorescence was not observed in co-transfected cells that had been exposed to the antagonist d-tubocurarine. These results demonstrate that the co-transfected cells express functional recombinant nAChR that are activated by nicotine and blocked by d-tubocurarine.

EXAMPLE 6

Characterization of Cell Lines Expressing Human Neuronal nAChRs

Recombinant cell lines generated by transfection with DNA encoding human neuronal nAChRs, such as those described in Example 3, can be further characterized using one or more of the following methods.

A. Northern or Slot Blot Analysis for Expression of α- and/or β-subunit Encoding Messages Total RNA is isolated from ~$1 \times 10^7$ cells and 10–15 Ag of RNA from each cell type is used for Northern or slot blot hybridization analysis. The inserts from human neuronal nAChR-encoding plasmids can be nick-translated and used as probe. In addition, a fragment of the glycoraldehyde-3-phosphate dehydrogenase (GAPD) gene sequence (Tso et al.

(1985) Nucleic Acids Res. 13, 2485) can be nick-translated and used as a control probe on duplicate filters to confirm the presence or absence of RNA on each blot and to provide a rough standard for use in quantitating differences in α- or β-specific mRNA levels between cell lines. Typical Northern and slot blot hybridization and wash conditions are as follows:

hybridization in 5× SSPE, 5×Denhardt's solution, 0.2% SDS, 200 μg/ml denatured, sonicated herring sperm DNA, 50% formamide, at 42° C. followed by washing in 0.1× SSPE, 0.1% SDS, at 65° C.

B. Nicotine-binding Assay

Cell lines generated by transfection with human neuronal nAChR α- or α- and β-subunit-encoding DNA can be analyzed for their ability to bind nicotine, for example, as compared to control cell lines:

neuronally-derived cell lines PC12 (Boulter et al., (1986), supra; ATCC #CRL1721) and IMR32 (Clementi, et al. (1986); Irit. J. Neurochem. 47:291–297; ATCC #CCL127), and muscle-derived cell line BC3H1 (Patrick, et al., (1977); J. Biol. Chem. 252:2143–2153). Negative control cells (i.e., host cells from which the transfectants were prepared) are also included in the assay. The assay is conducted as follows:

Just prior to being assayed, transfected cells are removed from plates by scraping. Positive control cells used are PC12, BC3H1, and IMR32 (which had been starved for fresh media for seven days). Control cell lines are removed by rinsing in 37° C. assay buffer (50 mM Tris/HCl, 1 mM $MgCl_2$, 2 mM $CaCl_2$, 120 mM NaCl, 3 mM EDTA, 2 mg/ml BSA and 0.1 % aprotinin at pH7.4). The cells are washed and resuspended to a concentration of $1\times10^6/250 \mu l$. To each plastic assay tube is added 250 μl of the cell solution, 15 nM $^3$H-nicotine, with or without 1 mM unlabeled nicotine, and assay buffer to make a final volume of 500 μl. The assays for the transfected cell lines are incubated for 30 min at room temperature; the assays of the positive control cells are incubated for 2 min at 1° C. After the appropriate incubation time, 450 μl aliquots of assay volume are filtered through Whatman GF/C glass fiber filters which has been pretreated by incubation in 0.05% polyethyleneimine for 24 hours at 4° C. The filters are then washed twice, with 4 ml each wash, with ice cold assay buffer. After washing, the filters are dried, added to vials containing 5 ml scintillation fluid and radioactivity is measured.

C. $^{86}$Rb Ion-flux Assay

The ability of nicotine or nAChR agonists and antagonists to mediate the influx of $^{86}$Rb into transfected and control cells has been found to provide an indication of the presence of functional nAChRs on the cell surface. The $^{86}$Rb ion-flux assay is conducted as follows:

1. The night before the experiment, cells are plated at $2\times10^6$ per well (i.e., 2 ml per well) in a 6-well polylysine-coated plate.
2. The culture medium is decanted and the plate washed with 2 ml of assay buffer (50 mM HEPES, 260 mM sucrose, 5.4 mM KCl, 1.8 mM $CaCl_2$, 0.8 mM $MgSO_4$, 5.5. mM glucose) at room temperature.
3. The assay buffer is decanted and 1 ml of assay buffer, containing 3 μCi/ml $^{86}$Rb, with 5 mM ouabain and agonist or antagonist in a concentration to effect a maximum response, is added.
4. The plate is incubated on ice at 1° C. for 4 min.
5. The buffer is decanted into a waste container and each well was washed with 3 ml of assay buffer, followed by two washes of 2 ml each.
6. The cells are lysed with 2×0.5 ml of 0.2% SDS per well and transferred to a scintillation vial containing 5 ml of scintillation fluid.
7. The radioactivity contained in each vial is measured and the data calculated.

Positive control cells provided the following data in this assay:

| | PC12 | | IMR32 | |
|---|---|---|---|---|
| | $EC_{50}$ | Maximum response | $EC_{50}$ | Maximum response |
| Agonist | | | | |
| nicotine | 52 μM | 2.1X[a] | 18 μM | 7.7X[a] |
| CCh* | 35 μM | 3.3X[b] | 230 μM | 7.6X[c] |
| cytisine | 57 μM | 3.6X[d] | 14 μM | 10X[e] |
| Antagonist | | | | |
| d-tubocurarine | 0.81 μM | | 2.5 μM | |
| mecamylamine | 0.42 μM | | 0.11 μM | |
| hexamethonium | nd[f] | | 22 μM | |
| atropine | 12.5 μM | | 43 μM | |

*CCh = carbamylcholine
[a]200 μM nicotine
[b]300 μM CCh
[c]3 mM CCh
[d]1 mM cytisine
[e]100 μM cytisine
[f]nd = not determined D. Electrophysiological Analysis of Mammalian Cells Transfected with Human Neuronal nAChR Subunit-encoding DNA Electrophysiological measurements may be used to assess the activity of recombinant receptors or to assess the ability of a test compound to potentiate, antagonize or otherwise modulate the magnitude and duration of the flow of cations through the ligand-gated recombinant nAChR. The function of the expressed neuronal nAChR can be assessed by a variety of electrophysiological techniques, including two-electrode voltage clamp and patch clamp methods. The cation-conducting channel intrinsic to the nAChR opens in response to acetylcholine (ACh) or other nicotinic cholinergic agonists, permitting the flow of transmembrane current carried predominantly by sodium and potassium ions under physiological conditions. This current can be monitored directly by voltage clamp techniques. In preferred embodiments, transfected mammalian cells or injected oocytes are analyzed electrophysiologically for the presence of nAChR agonist-dependent currents.

While the invention has been described in detail with reference to certain preferred embodiments thereof, it will be understood that modifications and variations are within the spirit and scope of that which is described and claimed.

Summary of Sequences

Sequence ID No. 1 is a nucleotide sequence encoding an $\alpha_6$ subunit of human neuronal nicotinic acetylcholine receptor, and the deduced amino acid sequence thereof.

Sequence ID No. 2 is the amino acid sequence of the $\alpha_6$ subunit of human neuronal nicotinic acetylcholine receptor set forth in Sequence ID No. 1.

Sequence ID No. 3 is a nucleotide sequence encoding a $\beta_3$ subunit of human neuronal nicotinic acetylcholine receptor, and the deduced amino acid sequence thereof.

Sequence ID No. 4 is the amino acid sequence of the $\beta_3$ subunit of human neuronal nicotinic acetylcholine receptor set forth in Sequence ID No. 3.

That which is claimed:

1. An isolated DNA molecule, comprising a sequence of nucleotides that encode an $\alpha_6$-subunit of a human neuronal nicotinic acetylcholine receptor, wherein the sequence of nucleotides encoding the $\alpha_6$ subunit is selected from the group consisting of:
   a) a sequence of nucleotides that encodes a human $\alpha_6$ subunit and comprises the coding portion of the sequence of nucleotides as set forth in SEQ ID NO: 1;
   b) a sequence of nucleotides that encodes a human $\alpha_6$ subunit that comprises the sequence of amino acids as set forth in SEQ ID NO: 2; and
   c) a sequence of nucleotides which is degenerate as a result of the genetic code to the sequence of nucleotides as set forth in any of (a) or (b).

2. The DNA molecule of claim 1, wherein the DNA molecule encodes the sequences of amino acids set forth in SEQ ID NO:2.

3. The DNA molecule of claim 1, wherein the DNA molecule encoding the $\alpha_6$-subunit comprises nucleotides 143–1624 as set forth in SEQ ID NO: 1.

4. An isolated DNA molecule, comprising a sequence of nucleotides that encode a full length $\beta_3$ subunit of a human neuronal nicotinic acetylcholine receptor, wherein the sequence of nucleotides encoding the $\beta_3$ subunit is selected from the group consisting of:
   a) a sequence of nucleotides that encodes a human $\beta_3$ subunit and comprises the coding sequence of nucleotides as set forth in SEQ ID NO: 3;
   b) a sequence of nucleotides that encodes a human $\beta_3$ subunit that comprises the sequence of amino acids as set forth in SEQ ID NO:. 4; and
   c) a sequence of nucleotides which is degenerate as a result of the genetic code to the sequence of nucleotides as set forth in any of (a) or (b).

5. The DNA molecule of claim 4 that encodes the sequence of amino acids set forth in SEQ ID NO:4.

6. The DNA molecule of claim 4, comprising the nucleotides 98–1472 as set forth in SEQ ID NO:3.

7. Isolated cells containing the DNA molecule of claim 1, wherein the DNA molecule encodes an $\alpha_6$ subunit of a human neuronal nicotinic acetylcholine receptor and comprises the sequence of nucleotides set forth in SEQ. ID. NO. 1.

8. The cells of claim 7, further containing a DNA molecule encoding a $\beta$ subunit of human neuronal nicotinic acetylcholine receptor.

9. The cells of claim 8, wherein the $\beta$ subunit is $\beta_3$; and the $\beta_3$ subunit is encoded by a sequence of nucleotides selected from the group consisting of:
   a) a sequence of nucleotides that encodes a human $\beta_3$ subunit and comprises the coding sequence of the sequence of nucleotides as set forth in SEQ ID NO: 3;
   b) a sequence of nucleotides that encodes a human $\beta_3$ subunit that comprises the sequence of amino acids as set forth in SEQ ID NO: 4; and c) a sequence of nucleotides which is degenerate as a result of the genetic code to the sequence of nucleotides as set forth in any of (a), or (b).

10. Isolated cells containing the DNA molecule of claim 4, wherein the DNA molecule encodes an $\beta_3$ subunit of a human neuronal nicotinic acetylcholine receptor and comprises the sequence of nucleotides set forth in SEQ. ID. NO. 3.

11. Isolated mRNA transcribed from the DNA of claim 1.

12. Isolated mRNA transcribed from the DNA of claim 4.

13. Isolated cells containing the mRNA of claim 11, wherein the mRNA is heterologous to the cells.

14. Isolated cells containing the mRNA of claim 12, wherein the mRNA is heterologous to the cells.

15. The cells of claim 13, wherein said cells further contain mRNA encoding a beta subunit of a human neuronal nicotinic acetylcholine receptor.

16. The cells of claim 14, wherein said cells further contain mRNA encoding an alpha subunit of a human neuronal nicotinic acetylcholine.

17. The DNA molecule of claim 1 encoding an $\alpha_6$ subunit of a human neuronal nicotinic acetylcholine receptor, wherein the $\alpha_6$ subunit comprises the sequence of amino acids set forth in SEQ ID No. 2.

18. The DNA molecule of claim 17, comprising the sequence of nucleotides set forth as nucleotides 143–1624 in SEQ ID No. 1.

19. The DNA molecule of claim 4 encoding a $\beta_3$ subunit of a human neuronal nicotinic acetylcholine receptor, wherein the $\beta_3$ subunit comprises the sequence of amino acids set forth in SEQ ID No. 4.

20. The DNA molecule of claim 19, comprising the sequence of nucleotides set forth as nucleotides 98–1472 in SEQ ID No. 3.

21. The DNA molecule of claim 1, comprising the sequence of nucleotides set forth in SEQ ID No. 1.

22. The DNA molecule of claim 4, comprising the sequence of nucleotides set forth in SEQ ID No.3.

23. The cells of claim 13 that express neuronal nicotinic acetylcholine receptors.

24. The cells of claim 14 that express neuronal nicotinic acetylcholine receptors.

25. The DNA molecule of claim 1 that is isolated from a neuronal cDNA library.

26. The DNA molecule of claim 4 that is isolated from a neuronal cDNA library.

27. An isolated DNA molecule, comprising a sequence of nucleotides that encodes amino acids 1–28 of SEQ. ID No. 4.

28. An isolated DNA molecule, comprising a sequence of nucleotides that encodes amino acids. 1–20of SEQ ID. No. 4.

29. An isolated DNA molecule, comprising nucleotides 98–202 set forth in SEQ ID No. 3.

30. The isolated cells according to claim 7, wherein the cells are selected from the group consisting of bacterial cells, eukaryotic cells and amphibian oocytes.

31. The isolated cells according to claim 10, wherein the cells are selected from the group consisting of bacterial cells, eukaryotic cells and amphibian oocytes.

32. Isolated cells containing the DNA molecule of claim 1, wherein the DNA molecule encodes an $\alpha_6$ subunit of a human neuronal nicotinic acetylcholine receptor and comprises a sequence of nucleotides that hybridize under conditions of high stringency to any probe complementary to at least 27 contiguous bases from the coding portion of the sequence of nucleotides set forth in SEQ. ID. NO. 1.

33. The isolated cells according to claim 32, wherein the cells are selected from the group consisting of bacterial cells, eukaryotic cells and amphibian oocytes.

34. Isolated cells containing the DNA molecule of claim 1, wherein the DNA molecule encodes an $\alpha_6$ subunit of a human neuronal nicotinic acetylcholine receptor having an amino acid sequence as set forth in SEQ. ID. NO. 2.

35. The isolated cells according to claim 34, wherein the cells are selected from the group consisting of bacterial cells, eukaryotic cells and amphibian oocytes.

36. Isolated cells containing the DNA molecule of claim 1, wherein the DNA molecule encodes an $\alpha_6$ subunit of a human neuronal nicotinic acetylcholine receptor and comprises a sequence of nucleotides that are degenerate with a sequence of nucleotides that hybridize under conditions of high stringency to any probe that is complementary to at least 27 contiguous bases from the coding portion of the sequence of nucleotides set forth in SEQ. ID. NO. 1.

37. The isolated cells according to claim 36, wherein the cells are selected from the group consisting of bacterial cells, eukaryotic cells and amphibian oocytes.

38. Isolated cells containing the DNA molecule of claim 4, wherein the DNA molecule encodes an $\beta_3$ subunit of a human neuronal nicotinic acetylcholine receptor and comprises a sequence of nucleotides that hybridize under conditions of high stringency to DNA complementary to the entire coding portion of the sequence of nucleotides set forth in SEQ. ID. NO. 3.

39. The isolated cells according to claim 38, wherein the cells are selected from the group consisting of bacterial cells, eukaryotic cells and amphibian oocytes.

40. Isolated cells containing the DNA molecule of claim 4, wherein the DNA molecule encodes an $\beta_3$ subunit of a human neuronal nicotinic acetylcholine receptor having an amino acid sequence as set forth in SEQ. ID. NO. 4.

41. The isolated cells according to claim 40, wherein the cells are selected from the group consisting of bacterial cells, eukaryotic cells and amphibian oocytes.

42. Isolated cells containing the DNA molecule of claim 4, wherein the DNA molecule encodes an $\beta_3$ subunit of a human neuronal nicotinic acetylcholine receptor and comprises a sequence of nucleotides that are degenerate with a sequence of nucleotides that hybridize under conditions of high stringency to DNA complementary to the entire coding portion of the sequence of nucleotides set forth in SEQ. ID. NO. 3.

43. The isolated cells according to claim 42, wherein the cells are selected from the group consisting of bacterial cells, eukaryotic cells and amphibian oocytes.

* * * * *